US011660453B2

(12) United States Patent
Vallejo et al.

(10) Patent No.: US 11,660,453 B2
(45) Date of Patent: *May 30, 2023

(54) METHOD AND APPARATUS FOR MULTI MODAL ELECTRICAL MODULATION OF PAIN

(71) Applicant: Medtronic SG, LLC, Minneapolis, MN (US)

(72) Inventors: Ricardo Vallejo, Bloomington, IL (US); David Leonardo Cedeno, Normal, IL (US); Ramsin M. Benyamin, Bloomington, IL (US)

(73) Assignee: Medtronic SG, LLC, Minneapolis, MN (US)

( * ) Notice: Subject to any disclaimer, the term of this patent is extended or adjusted under 35 U.S.C. 154(b) by 205 days.

This patent is subject to a terminal disclaimer.

(21) Appl. No.: 17/106,589

(22) Filed: Nov. 30, 2020

(65) Prior Publication Data

US 2021/0093865 A1 Apr. 1, 2021

Related U.S. Application Data

(63) Continuation of application No. 16/055,787, filed on Aug. 6, 2018, now Pat. No. 10,850,102, which is a
(Continued)

(51) Int. Cl.
*A61N 1/36* (2006.01)
*A61N 1/05* (2006.01)
*A61N 2/00* (2006.01)

(52) U.S. Cl.
CPC ....... *A61N 1/36071* (2013.01); *A61N 1/0551* (2013.01); *A61N 1/36062* (2017.08);
(Continued)

(58) Field of Classification Search
None
See application file for complete search history.

(56) References Cited

U.S. PATENT DOCUMENTS

| 2,622,601 | A | 12/1952 | Nemec |
| 3,774,620 | A | 11/1973 | Hansjurgens |

(Continued)

FOREIGN PATENT DOCUMENTS

| EP | 2630984 A1 | 8/2013 |
| EP | 2207587 B1 | 4/2015 |

(Continued)

OTHER PUBLICATIONS

Al-Kaisy et al.; "10kHz High-Frequency Spinal Cord Stimulation for Chronic Axial Low Back Pain in Patients with No History of Spinal Surgery: A Preliminary, Prospective, Open Label and Proof-of-Concept Study"; Neuromodulation; Oct. 18, 2015, pp. 63-70.
(Continued)

*Primary Examiner* — Ankit D Tejani
(74) *Attorney, Agent, or Firm* — Shumaker & Sieffert, P.A.

(57) ABSTRACT

Apparatus and methods for managing pain uses separate varying electromagnetic fields, with a variety of temporal and amplitude characteristics, which are applied to a particular neural structure to modulate glial and neuronal interactions as a mechanism for relieving chronic pain. In another embodiment, a single composite modulation/stimulation signal which has rhythmically varying characteristics is used to achieve the same results as separate varying electromagnetic fields. Also, disclosed is an apparatus and method for modulating the expression of genes involved in diverse pathways including inflammatory/immune system mediators, ion channels and neurotransmitters, in both the Spinal Cord (SC) and Dorsal Root Ganglion (DRG) where such expression modulation is caused by spinal cord stimulation
(Continued)

or peripheral nerve stimulation using the disclosed apparatus and techniques. In one embodiment of multimodal modulation therapy, the prime signal may be monophasic, or biphasic, in which the polarity of the first phase of the biphasic prime signal may be either cathodic or anodic while the tonic signal may be either monophasic, or biphasic, with the polarity of the first phase of the biphasic tonic signal being either cathodic or anodic.

20 Claims, 22 Drawing Sheets

Related U.S. Application Data continuation-in-part of application No. 15/075,550, filed on Mar. 21, 2016, now Pat. No. 10,039,930.

(60) Provisional application No. 62/196,030, filed on Jul. 23, 2015, provisional application No. 62/135,999, filed on Mar. 20, 2015.

(52) U.S. Cl.
CPC ..... *A61N 1/36192* (2013.01); *A61N 1/36196* (2013.01); *A61N 2/002* (2013.01); *A61N 2/008* (2013.01)

(56) References Cited

U.S. PATENT DOCUMENTS

| | | |
|---|---|---|
| 4,023,574 A | 5/1977 | Nemec |
| 4,071,033 A | 1/1978 | Nawracaj |
| 4,535,777 A | 8/1985 | Castel |
| 4,960,124 A | 10/1990 | Masaki |
| 5,224,477 A | 7/1993 | Itoh |
| 5,269,304 A | 12/1993 | Mattews |
| 5,324,317 A | 6/1994 | Reiss |
| 5,683,422 A | 11/1997 | Rise |
| 5,716,377 A | 2/1998 | Rise et al. |
| 5,776,170 A | 7/1998 | MacDonald et al. |
| 5,791,344 A | 8/1998 | Schulman et al. |
| 5,833,709 A | 11/1998 | Rise et al. |
| 5,938,690 A | 8/1999 | Law et al. |
| 5,948,007 A | 9/1999 | Starkebaum et al. |
| 5,983,141 A | 11/1999 | Sluijter et al. |
| 6,002,964 A | 12/1999 | Feler et al. |
| 6,066,163 A | 5/2000 | John |
| 6,067,470 A | 5/2000 | Mower |
| 6,246,912 B1 | 6/2001 | Sluijter et al. |
| 6,366,813 B1 | 4/2002 | DiLorenzo |
| 6,393,325 B1 | 5/2002 | Mann |
| 6,463,328 B1 | 10/2002 | John |
| 6,480,743 B1 | 11/2002 | Kirpatrick |
| 6,505,078 B1 | 1/2003 | King et al. |
| 6,539,263 B1 | 3/2003 | Schiff |
| 6,584,358 B2 | 6/2003 | Carter et al. |
| 6,591,138 B1 | 7/2003 | Fischell |
| 6,662,053 B2 | 12/2003 | Borkan |
| 6,665,562 B2 | 12/2003 | Gluckman |
| 6,826,429 B2 | 11/2004 | Johnson |
| 6,923,784 B2 | 8/2005 | Stein |
| 6,941,171 B2 | 9/2005 | Mann |
| 7,149,574 B2 | 12/2006 | Yun et al. |
| 7,228,178 B2 | 6/2007 | Carroll et al. |
| 7,877,136 B1 | 1/2011 | Moffitt et al. |
| 8,209,021 B2 | 6/2012 | Alataris et al. |
| 8,359,102 B2 | 1/2013 | Alataris et al. |
| 8,364,273 B2 | 1/2013 | De Ridder |
| 8,380,316 B2 | 2/2013 | Hagedorn et al. |
| 8,380,318 B2 | 2/2013 | Kishawi et al. |
| 8,583,239 B2 | 11/2013 | Pless et al. |
| 8,774,927 B2 | 7/2014 | De Ridder |
| 8,788,044 B2 | 7/2014 | John |
| 8,977,363 B2 | 3/2015 | Carroll et al. |
| 8,977,373 B2 | 3/2015 | Felty et al. |
| 9,138,582 B2 | 9/2015 | Doan et al. |
| 9,174,053 B2 | 11/2015 | Zhu |
| 9,462,398 B2 | 10/2016 | De Ridder |
| 9,572,984 B2 | 2/2017 | Hou et al. |
| 9,895,539 B1 | 2/2018 | Heit et al. |
| 9,962,547 B2 | 5/2018 | Vallejo et al. |
| 10,039,930 B2 | 8/2018 | Vallejo et al. |
| 10,188,864 B2 | 1/2019 | John |
| 10,583,299 B2 | 3/2020 | John |
| 10,850,102 B2 | 12/2020 | Vallejo et al. |
| 2002/0022866 A1 | 2/2002 | Borkan |
| 2002/0038137 A1 | 3/2002 | Stein |
| 2002/0072770 A1 | 6/2002 | Pless |
| 2002/0169485 A1 | 11/2002 | Pless |
| 2003/0028072 A1 | 2/2003 | Fischell |
| 2003/0078633 A1 | 4/2003 | Firlik |
| 2003/0135248 A1 | 7/2003 | Stypulkowski |
| 2003/0149457 A1 | 8/2003 | Tcheng |
| 2003/0204226 A1 | 10/2003 | Acosta |
| 2004/0002635 A1 | 1/2004 | Hargrove |
| 2004/0127953 A1 | 7/2004 | Kilgore et al. |
| 2004/0167584 A1 | 8/2004 | Carroll et al. |
| 2004/0172089 A1 | 9/2004 | Whitehurst |
| 2004/0210270 A1 | 10/2004 | Erickson |
| 2004/0210271 A1 | 10/2004 | Campen |
| 2004/0215286 A1 | 10/2004 | Stypulkowski |
| 2004/0267330 A1 | 12/2004 | Lee et al. |
| 2005/0021104 A1 | 1/2005 | DiLorenzo |
| 2005/0033381 A1 | 2/2005 | Carter et al. |
| 2005/0049649 A1 | 3/2005 | Luders |
| 2005/0049651 A1 | 3/2005 | Whitehurst |
| 2005/0065575 A1 | 3/2005 | Dobak |
| 2005/0081847 A1 | 4/2005 | Lee |
| 2005/0149148 A1 | 7/2005 | King |
| 2005/0154425 A1 | 7/2005 | Boveja |
| 2005/0171587 A1 | 8/2005 | Daglow |
| 2005/0240242 A1 | 10/2005 | DiLorenzo |
| 2005/0245993 A1 | 11/2005 | Varrichio |
| 2005/0246003 A1 | 11/2005 | Black |
| 2006/0004422 A1 | 1/2006 | De Ridder |
| 2006/0009820 A1 | 1/2006 | Royle |
| 2006/0015153 A1 | 1/2006 | Gliner et al. |
| 2006/0074456 A1 | 4/2006 | Pyles et al. |
| 2006/0095088 A1 | 5/2006 | De Ridder |
| 2006/0100671 A1 | 5/2006 | Ridder |
| 2006/0116742 A1 | 6/2006 | De Ridder |
| 2006/0149337 A1 | 7/2006 | John |
| 2006/0184211 A1 | 8/2006 | Gaunt et al. |
| 2007/0060954 A1 | 3/2007 | Cameron et al. |
| 2007/0073354 A1 | 3/2007 | Knudson et al. |
| 2007/0083240 A1 | 4/2007 | Peterson et al. |
| 2007/0150034 A1 | 6/2007 | Rooney et al. |
| 2007/0213771 A1 | 9/2007 | Spinner et al. |
| 2007/0265681 A1 | 11/2007 | Gerber et al. |
| 2009/0018617 A1 | 1/2009 | Skelton et al. |
| 2009/0024187 A1 | 1/2009 | Erickson et al. |
| 2010/0057178 A1 | 3/2010 | Simon |
| 2010/0249875 A1 | 9/2010 | Kisha Wi et al. |
| 2011/0106208 A1 | 5/2011 | Faltys et al. |
| 2011/0184488 A1 | 7/2011 | De Ridder |
| 2011/0251229 A1 | 10/2011 | Watkins et al. |
| 2012/0016438 A1 | 1/2012 | Alataris et al. |
| 2012/0109020 A1 | 5/2012 | Wagner et al. |
| 2012/0277621 A1 | 11/2012 | Gerber et al. |
| 2012/0277823 A1 | 11/2012 | Gerber et al. |
| 2012/0310140 A1 | 12/2012 | Kramer et al. |
| 2013/0035745 A1 | 2/2013 | Ahmed et al. |
| 2013/0211477 A1 | 8/2013 | Cullen et al. |
| 2013/0303828 A1 | 11/2013 | Hargrove |
| 2013/0304159 A1 | 11/2013 | Simon et al. |
| 2013/0325084 A1 | 12/2013 | Lee |
| 2014/0207203 A1 | 7/2014 | Ternes et al. |
| 2014/0257428 A1 | 9/2014 | Zhu |
| 2014/0277265 A1 | 9/2014 | Khalil et al. |
| 2014/0330345 A1 | 11/2014 | John |
| 2015/0217117 A1 | 8/2015 | Hershey |
| 2016/0008604 A1 | 1/2016 | Doan et al. |

(56) References Cited

U.S. PATENT DOCUMENTS

| | | |
|---|---|---|
| 2016/0106985 A1 | 4/2016 | Zhu |
| 2016/0220813 A1 | 8/2016 | Edgerton et al. |
| 2016/0271413 A1 | 9/2016 | Vallejo et al. |
| 2018/0028812 A1 | 2/2018 | Vallejo et al. |
| 2018/0056073 A1 | 3/2018 | Torgerson |
| 2018/0243562 A1 | 8/2018 | Vallejo et al. |
| 2018/0243563 A1 | 8/2018 | Vallejo et al. |
| 2018/0250513 A1 | 9/2018 | Vallejo et al. |
| 2020/0164213 A1 | 5/2020 | John |
| 2020/0171308 A1 | 6/2020 | Vallejo et al. |

FOREIGN PATENT DOCUMENTS

| | | |
|---|---|---|
| EP | 2853285 A1 | 4/2015 |
| EP | 3156099 B1 | 6/2018 |
| WO | 199519804 | 7/1995 |
| WO | WO 9843700 A1 | 10/1998 |
| WO | WO 2004007018 A1 | 1/2004 |
| WO | WO 2006007048 A3 | 1/2006 |
| WO | WO 2006057734 A1 | 6/2006 |
| WO | WO 2007103324 A1 | 9/2007 |
| WO | WO 2009061813 A1 | 5/2009 |
| WO | 2009139968 A2 | 11/2009 |
| WO | WO 2016154091 A1 | 9/2016 |

OTHER PUBLICATIONS

Al-Kaisy et al.; "Sustained Effectiveness of 10 kHz High-Frequency Spinal Cord Stimulation for Patients with Chronic, Low Back Pain: 24-Month Results of a Prospective Multicenter Study"; Pain Medicine; 15; pp. 347-354; Mar. 2014.

Barr, et al., "Electrophysiological interaction through the interstitial space between adjacent unmyelinated parallel fibers" May 1992, Biophys J61, pp. 1164-1175.

Basser, et al., "New currents in electrical stimulation of excitable tissues" (2000) Annu Rev Biomed Eng 2, 377-397. (Applicant points out, in accordance with MPEP 609.04(a), that the year of publication, 2000 is sufficiently earlier than the effective U.S. filing date, so that the particular month of publication is not in issue.).

Bawin, et al., "Effects of modulated very high frequency fields on specific brain rhythms in cats" Aug. 30, 1973, Brain Res 58, pp. 365-384.

Benabid, et al., "Therapeutic electrical stimulation of the central nervous system", C R Biol 328, 177-186, Feb. 2005.

Benyamin et al.; "A Case of Spinal Cord Stimulation in Raynaud's Phenomenon: Can Subthreshold Sensory Stimulation Have an Effect?"; Pain Physician; 10; pp. 473-478; May 2007.

Boston Scientific; "Precision Spinal Cord Stimulator System Clinical Manual"; 91083273-01 Rev A; pp. 1-74; (2015); https://www.uhms.org/images/MEDFAQs/9108327301_RevA_Precision_Spinal_Cord_Stimulator_System_Clinician_Manua.pdf (Applicant points out, in accordance with MPEP 609.04(a), that the year of publication, 2015 is sufficiently earlier than the effective U.S. filing date, so that the particular month of publication is not in issue.).

Brasil-Neto et al., "Experimental therapy of epilepsy with transcranial magnetic stimulation: lack of additional benefit with prolonged treatment" Mar. 2004, Arq Neuropsiquiatr 62, pp. 21-25.

Bruet, et al., "High frequency stimulation of the subthalamic nucleus increases the extracellular contents of striatal dopamine in normal and partially dopaminergic denervated rats" Jan. 2001, J Neuropathol Exp Neurol 60, pp. 15-24.

Bruet, et al., "Neurochemical mechanisms induced by high frequency stimulation of the subthalamic nucleus: increase of extracellular striatal glutamate and GABA in normal and hemiparkinsonian ratS" Dec. 2003, J Neuropathol Exp Neurol 62, pp. 1228-1240.

Butt et al.; "Histological Findings Using Novel Stimulation Parameters in a Caprine Model"; Ref. F702) from Poster Sessions; European Journal of Pain Supplements; 5; p. 188; (2011) (Applicant points out, in accordance with MPEP 609.04(a), that the year of publication, 2011, is sufficiently earlier than the effective U.S. filing date, so that the particular month of publication is not in issue.).

Cemazar, et al, "Electrochemotherapy of tumours resistant to cisplatin: a study in a murine tumour model" (2001) Eur J Cancer 37, pp. 1166-1172, Jun. 2001.

Chakravarthy et al., "Mechanism of Action in Burst Spinal Cord Stimulation: Review and Recent Advances," Pain Medicine, downloaded on Dec. 16, 2019, 13 pp.

Ciria, et al., "Antitumor effectiveness of different amounts of electrical charge in Ehrlich and fibrosarcoma Sa-37 tumors" (2004) BMC Cancer 4, 87, Nov. 2004, 10 pp.

Collins English Dictionary; definition of "in place of"; one page; accessed May 19, 2020; https://www.collinsdictionary.com/dictionary/english/in-place-of.

Crapanzano et al.; "High Frequency Spinal Cord Stimulation for Complex Regional Pain Syndrome: A Case Report"; Pain Physician; 19; pp. E177-E182; Dec. 31, 2016.

Cucullo, et al., "Very low intensity alternating current decreases cell proliferation" (2005) Glia 51, pp. 65-72, Mar. 18, 2005.

D'Arcangelo, et al., "Repetitive low-frequency stimulation reduces epileptiform synchronization in limbic neuronal networks" (2005) Neurobiol Dis 19, 119-128; Jun.-Jul. 2005.

Deurloo, et al., "The effect of subthreshold prepulses on the recruitment order in a nerve trunk analyzed in a simple and a realistic volume conductor model" (2001) Biol Cybern 85, 281-291, Oct. 2001.

Dinner, "Effect of sleep on epilepsy" (2002) J Clin Neurophysiol 19, pp. 504-513, Dec. 2002.

Eddicks et al.; "Thoracic Spinal Cord Stimulation Improves Functional Status and Relieves Symptoms in Patients with Refractory Angina Pectoris: the first placebo-controlled randomised study"; Heart; 93; pp. 585-590; Jan. 19, 2007.

Faurie, et al., "Effect of electric field vectoriality on electrically mediated gene delivery in mammalian cells" (2004) Biochim Biophys Acta 1665, pp. 92-100, Oct. 2004.

Gerloff, et al., "Inhibitory influence of the ipsilateral motor cortex on responses to stimulation of the human cortex and pyramidal tract" (1998) J Physiol 510 (Pt 1), pp. 249-259, Jul. 1998.

Gerloff, et al., "Stimulation over the human supplementary motor area interferes with the organization of future elements in complex motor sequences" (1997) Brain 120 (Pt 9), pp. 1587-1602, Oct. 1997.

Goodman, et al., "Preemptive low-frequency stimulation decreases the incidence of amygdala-kindled seizures" (2005) Epilepsia 46, pp. 1-7, Jan. 2005.

Graham-Jones, et al., "Low-frequency septal stimulation increases tyrosine hydroxylase activity in the hippocampus" (1985) Pharmacol Biochem Behav 23, pp. 489-493, Oct. 1985.

Gray, et al., "Resistance to extinction after partial reinforcement training with blocking of the hippocampal theta rhythm by septal stimulation" (1972) Physiol Behav 8, pp. 497-502, Mar. 1972.

Kinfe et al., "Burst Spinal Cord Stimulation Increases Peripheral Antineuroinflammatory Interleukin 10 Levels in Failed Back Surgery Syndrome Patients With Predominant Back Pain," Jan. 3, 2017, 9 pp.

Hoekema, et al., "Multigrid solution of the potential field in modeling electrical nerve stimulation" (1998) Comput Biomed Res 31, pp. 348-362. (Applicant points out, in accordance with MPEP 609.04(a), that the year of publication, 1998 is sufficiently earlier than the effective U.S. filing date, so that the particular month of publication is not in issue.).

Holsheimer, et al., "Clinical evaluation of paresthesia steering with a new system for spinal cord stimulation" (1998) Neurosurgery 42, 541-547; discussion 547-549, Mar. 1998, 11 pp.

Holsheimer, et al., "Contact combinations in epidural spinal cord stimulation. A comparison by computer modeling" (1991) Stereotact Funct Neurosurg 56, pp. 220-233 (Applicant points out, in accordance with MPEP 609.04(a), that the year of publication, 1991 is sufficiently earlier than the effective U.S. filing date, so that the particular month of publication is not in issue.).

Holsheimer, et al., "Effect of anode-cathode configuration on paresthesia coverage in spinal cord stimulation" (1997) Neurosurgery 41, 654-659; discussion 659-660, Sep. 1997, 14 pp.

(56) References Cited

OTHER PUBLICATIONS

Holsheimer, et al., "Effects of electrode geometry and combination on nerve fibre selectivity in spinal cord stimulation" (1995) Med Biol Eng Comput 33, pp. 676-682, Sep. 1995.
Holsheimer, et al., "How do geometric factors influence epidural spinal cord stimulation? A quantitative analysis by computer modeling" (1991) Stereotact Funct Neurosurg 56, pp. 234-249 (Applicant points out, in accordance with MPEP 609.04(a), that the year of publication, 1991, is sufficiently earlier than the effective U.S. filing date, so that the particular month of publication is not in issue.).
Holsheimer, et al., "Optimum electrode geometry for spinal cord stimulation: the narrow bipole and tripole" (1997) Med Biol Eng Comput 35, pp. 493-497, Sep. 1997.
Holt, et al., "Proactive behavioral effects of theta-blocking septal stimulation in the rat" (1983) Behav Neural Biol 39, pp. 7-21, vol. 39, Issue 1, Sep. 1983.
Holt, et al., "Proactive behavioral effects of theta-driving septal stimulation on conditioned suppression and punishment in the rat" (1985) Behav Neurosci 99, pp. 60-74, Feb. 1985.
Irnich, "Paradigm shift in lead design" (1999) Pacing Clin Electrophysiol 22, pp. 1321-1332, Sep. 1999.
Iyer, et al., "Priming stimulation enhances the depressant effect of low-frequency repetitive transcranial magnetic stimulation" (2003) J Neurosci 23, pp. 10867-10872, Nov. 26, 2003.
John, et al., "An exploration of the functional relationship between electroencephalographic potentials and differential inhibition" (1961) Ann N Y Acad Sci 92, pp. 1160-1182, Jul. 1961.
Kapural et al.; "Comparison of 10-kHz High-Frequency and Traditional Low-Frequency Spinal Cord Stimulation for the Treatment of Chronic Back and Leg Pain: 24-Month Results From a Multicenter, Randomized, Controlled Pivotal Trial"; Neurosurgery; 79(5); pp. 667-677; Nov. 2016.
Kapural et al.; "Novel 10-kHz High-frequency Therapy (HF10 Therapy) Is Superior to Traditional Low-frequency Spinal Cord Stimulation for the Treatment of Chronic Bank and Leg Pain"; Anesthesiology; 123; pp. 851-860; Oct. 2015.
Kasteleijn-Nolst, et al., "The impact of subclinical epileptiform discharges on complex tasks and cognition: relevance for aircrew and air traffic controllers" (2005) Epilepsy Behav 6, pp. 31-34, Feb. 2005.
Katayama, et al., "Deep brain and motor cortex stimulation for post-stroke movement disorders and post-stroke pain" (2003) Acta Neurochir Suppl 87, pp. 121-123 (Applicant points out, in accordance with MPEP 609.04(a), that the year of publication, 2003 is sufficiently earlier than the effective U.S. filing date so that the particular month of publication is not in issue.).
Kilgore et al.; "Nerve Conduction Block Utilising High-Frequency Alternating Current"; Med. Biol. Eng. Comput.; 42; pp. 394-406; May 2004.
Kilgore, et al.; "Reversible Nerve Conduction Block Using Kilohertz Frequency Alternating Current"; Neuromodulation; 17(3); pp. 242-255; Apr. 2014.
Kim et al., "Uniformity of Current Density Under Stimulating Electrodes, Critical Reviews in Biomedical Engineering", vol. 17, Issue 6 (1990), pp. 585-619. (Applicant points out, in accordance with MPEP 609.04(a), that the year of publication, 1990 is sufficiently earlier than the effective U.S. filing date, so that the particular month of publication is not in issue.).
Kinoshita, et al., "Electric stimulation on human cortex suppresses fast cortical activity and epileptic spikes" Jun. 28, 2004, Epilepsia 45, pp. 787-791.
Kinoshita, et al., "Low-frequency repetitive transcranial magnetic stimulation for seizure suppression in patients with extratemporal lobe epilepsy—A pilot study" Sep. 2005, Seizure 14, pp. 387-392.
Kossoff, et al., "Effect of an external responsive neurostimulator on seizures and electrographic discharges during subdural electrode monitoring" Dec. 2004, Epilepsia 45, pp. 1560-1567.
Kovner, et al., "Disruption of short-term visual memory by electrical stimulation of inferotemporal cortex in the monkey" (1972) J Comp Physiol Psychol 81, pp. 163-172 (Applicant points out, in accordance with MPEP 609.04(a), that the year of publication, 1972 is sufficiently earlier than the effective U.S. filing date, so that the particular month of publication is not in issue.).
Krnjevic, et al., "Stimulation-evoked changes in extracellular K+ and Ca2+ in pyramidal layers of the rat's hippocampus" Dec. 1982, Can J Physiol Pharmacol 60, pp. 1643-1657.
Kumar et al., "The effects of spinal cord stimulation in neuropathic pain are sustained: a 24-month follow-up of the prospective randomized controlled multicenter trial of the effectiveness of spinal cord stimulation", Neurosurgery-online.com, vol. 63, No. 4. Oct. 2008, 9 pages.
Kuncel, et al., "Selection of stimulus parameters for deep brain stimulation" Nov. 2004, Clin Neurophysiol 115, pp. 2431-2441.
Lambru et al.; "Safety and Efficacy of Cervical 10kHz Spinal Cord Stimulation in Chronic Refractory Primary Headaches: a Retrospective Case Series"; The Journal of Headache and Pain; 17:66; 8 pages; Jul. 8, 2016.
Lempka et al.; "Computational Analysis of Kilohertz Frequency Spinal Cord Stimulation for Chronic Pain Management"; Anesthesiology; 122(6); pp. 1362-1376; Jun. 2015.
Lertmanorat, et al., "A novel electrode array for diameter-dependent control of axonal excitability: a simulation study" Jun. 21, 2004, IEEE Trans Biomed Eng 51, pp. 1242-1250.
Lertmanorat, et al., "Extracellular voltage profile for reversing the recruitment order of peripheral nerve stimulation: a simulation study" Nov. 17, 2004, J Neural Eng 1, pp. 202-211.
Levy, Robert M.; "The Need for Mechanism-Based Medicine in Neuromodulation"; Neuromodulation; 15; pp. 273-279; Jul. 2012.
Li et al., "An update on reactive astrocytes in chronic Pain," Journal of Neuroinflammation, Jul. 9, 2019, 13 pp.
Macmillan Dictionary (online); definition of "in place of"; 2 pages; accessed May 19, 2020; https://www.macmillandictionary.com/dictionary/british/in-place-of.
Manola, et al., "Modelling motor cortex stimulation for chronic pain control: electrical potential field, activating functions and responses of simple nerve fibre models" May 2005, Med Biol Eng Comput 43, pp. 335-343.
Matsuda, et al., "Epileptogenesis induced by alternate-site kindling in bilateral hippocampi" Mar. 2003, Epilepsia 44, pp. 292-298.
Mcintyre, et al., "Cellular effects of deep brain stimulation: model-based analysis of activation and inhibition" Apr. 1, 2004, J Neurophysiol 91, pp. 1457-1469.
Mcintyre, et al., "Electric field and stimulating influence generated by deep brain stimulation of the subthalamic nucleus" Mar. 2004, Clin Neurophysiol 115, pp. 589-595.
Mcintyre, et al., "Excitation of central nervous system neurons by nonuniform electric fields" Feb. 1999, Biophys J76, pp. 878-888.
Mcintyre, et al., "Extracellular stimulation of central neurons: influence of stimulus waveform and frequency on neuronal output" Oct. 2002, J Neurophysiol 88, pp. 1592-1604.
Mcintyre, et al., "Finite element analysis of the current-density and electric field generated by metal microelectrodes" Mar. 2001, Ann Biomed Eng 29, pp. 227-235.
Mcintyre, et al., "Selective microstimulation of central nervous system neurons" Mar. 2000, Ann Biomed Eng 28, pp. 219-233.
Menkes, et al., "Slow-frequency repetitive transcranial magnetic stimulation in a patient with focal cortical dysplasia" Epilepsia 41, pp. 240-242, Aug. 2, 2005.
Mie, et al., Induction of neural differentiation by electrically stimulated gene expression of NeuroD2. Feb. 2003, J Biotechnol 100, pp. 231-238.
Miklavcic, et al., "The effect of high frequency electric pulses on muscle contractions and antitumor efficiency in vivo for a potential use in clinical electrochemotherapy" Feb. 2005, Bioelectrochemistry 65, pp. 121-128.
Miklavcic, et al., "The importance of electric field distribution for effective in vivo electroporation of tissues" vol. 74, Issue 5, May 1998, Biophys J 74, pp. 2152-2158.
Misawa, et al., "Low-frequency transcranial magnetic stimulation for epilepsia partialis continua due to cortical dysplasia" vol. 234, Issues 1-2. Jul. 2005, J Neurol Sci 234, pp. 37-39.

(56) References Cited

OTHER PUBLICATIONS

Miyoshi, et al., "Proposal of a new method for narrowing and moving the stimulated region of cochlear implants: animal experiment and numerical analysis" Apr. 1999, IEEE Trans Biomed Eng 46, pp. 451-460.

Moro, et al., "The impact on Parkinson's disease of electrical parameter settings in STN stimulation" Sep. 2002, Neurology 59, pp. 706-713.

Mutani, et al., "Effect of low frequency caudate stimulation on the EEG of epileptic neocortex" Aug. 1969, Brain Res 14, pp. 749-753.

Nakagawa, et al., "Suppression of spontaneous epileptiform activity with applied currents". Dec. 1991, Brain Res 567, pp. 241-247.

Nakamura, "Two types of inhibitory effects upon brain stem reticular neurons by low frequency stimulation of raphe nucleus in the rat" Feb. 1977, Brain Res 93, pp. 140-144.

Nashold, Jr. et al.; "Dorsal Column Stimulation for Control of Pain"; J. Neurosurg.; 36; pp. 590-597; May 1972.

Neurosurgery Survival Guide—2016, http://neurosurgerysurvivalguide.com, 4 pages, downloaded on Jul. 15, 2020.

Nevro Fact Sheet; "HF10(TM) Therapy Fact Sheet"; Sep. 5, 2015 Rev A; https://sals3.patientpop.com/assets/docs/28990.pdf+&cd=1&hl=en&ct=clnk&gl=us, 4 pages.

Oakley et al.; "A New Spinal Cord Stimulation System Effectively Relieves Chronic, Intractable Pain: A Multicenter Prospective Clinical Study"; Neuromodulation: Technology at the Neural Interface; 10(3); pp. 262-278; Jan. 2007.

Oakley, John C.; "Spinal Cord Stimulation in Axial Low Back Pain: Solving the Dilemma"; Pain Medicine; vol. 7; pp. S58-S63; 2006, downloaded May 19, 2020.

Perruchoud et al.; "Analgesic Efficacy of High-Frequency Spinal Cord Stimulation: A Randomized Double-Blind Placebo-Controlled Study"; Neuromodulation; 16; pp. 363-369; Dec. 21, 2012.

Plonsey, et al., "Electric field stimulation of excitable tissue" (1995) IEEE Trans Biomed Eng 42, pp. 329-336, Apr. 1995.

Plonsey, et al., "Electric field stimulation of excitable tissue" (1998) IEEE Eng Med Biol Mag 17, pp. 130-137, Sep./Oct. 1998.

Porter et al, "Hippocampal Astrocytes In Situ Respond to Glutamate Released from Synaptic Terminals," The Journal of Neuroscience, Aug. 15, 1996, 9 pp.

Puc et al., "Techniques of signal generation required for electropermeabilization. Survey of electropermeabilization devices" (2004) Bioelectrochemistry 64, pp. 113-124, accepted Apr. 8, 2004.

Pucihar, et al., "The effect of pulse repetition frequency on the uptake into electropermeabilized cells in vitro with possible applications in electrochemotherapy" (2002) Bioelectrochemistry 57, pp. 167-172, Jun. 4, 2002.

Pumir, et al., "Effect of an externally applied electric field on excitation propagation in the cardiac muscle" (1994) Chaos 4, pp. 547-555, Jun. 4, 1998.

Rattay, et al., "Effective electrode configuration for selective stimulation with inner eye prostheses" (2004) IEEE Trans Biomed Eng 51, pp. 1659-1664, Sep. 2004.

Reddy et al.; "Comparison of Conventional and Kilohertz Frequency Epidural Stimulation in Patients Undergoing Trialing for Spinal Cord Stimulation: Clinical Considerations", World Neurosurg.; 88; pp. 586-591; Apr. 2016.

Robb et al.; "Transcutaneous Electrical Nerve Stimulation vs. Transcutaneous Spinal Electroanalgesia for Chronic Pain Associated with Breast Cancer"; Journal of Pain and Symptom Management; 33(4); pp. 410-419; vol. 33, No. 4. Apr. 2007.

Rossi, et al., "Reduction of cortical myoclonus-related epileptic activity following slow-frequency rTMS" (2004) Neuroreport 15, pp. 293-296, Oct. 6, 2003.

Santos-Anderson, et al., "Stimulation of rat medial or sulcal prefrontal cortex during passive avoidance learning selectively influences retention performance" (1976) Brain Res 103, pp. 243-259, accepted Jul. 21, 1975.

Satkauskas, et al., "Electrophoretic Component of Electric Pulses Determines the Efficacy of In Vivo DNA Electrotransfer" (2005) Human Gene Therapy 16: pp. 1194-1201, Oct. 2005.

Senza Omnia Stimulator for Chronic Pain, with Widest Frequency Range, FDA Approved ; Product Information from Medgadget; 5 pages; printed May 18, 2020; https://www.medadget.com./2019/11/senze-omnia-stimulator-for-chronic-pain-with-widest-frequency-range-fda-approved.html.

Sepulveda, et al., "Finite element analysis of current pathways with implanted electrodes" (1983) J Biomed Eng 5, pp. 41-48, Jan. 1983.

Shetty et al.; "The Successful Treatment of Post-Implantation Iatrogenic Neuropathic Pain With Target-Field Stimulation Using Existing Stimulating System"; Ref 701; from Poster Sessions/European Journal of Pain Supplements; 5; p. 188; (2011) (Applicant points out, in accordance with MPEP 609.04(a), that the year of publication, 2011, is sufficiently earlier than the effective U.S. filing date, so that the particular month of publication is not in issue.).

Sato et al., "Spinal cord stimulation reduces mechanical hyperalgesia and glial cell activation in animals with neuropathic pain," PMC Public Access, Feb. 1, 2015, 20 pp.

Scholz et al., "The neuropathic pain triad: neurons, immune cells and glia," Nature Neuroscience, vol. 10, No. 11, Nov. 2007, 8 pp.

Simpson, et al.; "A Randomized, Double-Blind, Crossover Study of the Use of Transutaneous Spinal Electroanalgesia in Patients with Pain from Chronic Critical Limb Ischemia"; Journal of Pain and Symptom Management; 28(5); pp. 511-516; Nov. 2004.

Skelton, et al., "Low-frequency stimulation of the perforant path produces long-term potentiation in the dentate gyms of unanesthetized rats" (1983) Can J Physiol Pharmacol 61, pp. 1156-1161, received Dec. 21, 1982.

St. Jude Medical, Product Information; "Eon Mini Rechargeable IPG"; 2 pages; https://pdf.medicalexpo.com/pdf/st-jude-medical/eon-mini-rechargeable-ipg/70886-94459.html.

Stephens et al., "RNA-seq of spinal cord from nerve-injured rats after spinal cord stimulation," Molecular Pain, Nov. 12, 2018, 13 pp.

Struijk, et al., "Theoretical performance and clinical evaluation of transverse tripolar spinal cord stimulation" (1998) IEEE Trans Rehabil Eng 6, pp. 277-285, Sep. 1998.

Struijk, et al., "Transverse tripolar spinal cord stimulation: theoretical performance of a dual channel system" (1996) Med Biol Eng Comput 34, pp. 273-279, final form received Oct. 26, 1995.

Susil, et al., "Separation between virtual sources modifies the response of cardiac tissue to field stimulation" (1999) J. Cardiovasc Electrophysiol 10, pp. 715-727, published Feb. 1999.

Sweet et al.; "Paresthesia-Free High-Density Spinal Cord Stimulation for Postlaminectomy Syndrome in a Prescreened Population: A Prospective Case Series"; Neuromodulation; 19; pp. 260-267; (2016).

Tai, et al., "Simulation of nerve block by high-frequency sinusoidal electrical current based on the Hodgkin-Huxley model" IEEE Trans Neural Syst Rehabil Eng. Sep. 2005; 13(3), pp. 415-422.

Tan et al.; "Intensity Modulation: A Novel Approach to Percept Control in Spinal Cord Stimulation"; Neuromodulation; 19; pp. 254-259; (2016), accepted Sep. 1, 2015.

Tawfik et al., "Deep Brain Stimulation Results in Local Glutamate and Adenosine Release: Investigation into the Role of Astrocytes," Neurosurgery, Aug. 2010, 17 pp.

Tergau, et al., "Low-frequency repetitive transcranial magnetic stimulation improves intractable epilepsy" (1999) Lancet 353, p. 2209, Jun. 26, 1999.

Thompson et al.; "A Double Blind Randomised Controlled Clinical Trial on the Effect of Transcutaneous Spinal Electroanalgesia (TSE) on Low Back Pain"; European Journal of Pain; 12; pp. 371-377; (2008), available online Sep. 7, 2007.

Tiede et al.; "Novel Spinal Cord Stimulation Parameters in Patients with Predominant Back Pain"; Neuromodulation; 16; pp. 370-375; accepted Jan. 3, 2013.

Ueno, et al., "Localized stimulation of neural tissues in the brain by means of paried configuration of time-varying magnetic fields" (1988) Journal of Applied Phys. 64, pp. 5862-5864, Nov. 15, 1988.

Van Buyten; "High-Frequency Spinal Cord Stimulation for the Treatment of Chronic Back Pain Patients: Results of a Prospective Multicenter European Clinical Study"; Neuromodulation; 16; pp. 59-66; Oct. 13, 2013.

Vedam-Mai et al., "Deep brain stimulation and the role of astrocytes," Molecular Psychiatry (2012) 17, 124-131, published online May 31, 2011, 8 pp.

(56) References Cited

OTHER PUBLICATIONS

Velisek, et al., "Low-frequency stimulation of the kindling focus delays basolateral amygdala kindling in immature rats" (2002) Neurosci Lett 326, pp. 61-63, Feb. 18, 2002.
Velisek, et al., "Lowering of extracellular pH suppresses low-Mg(2+)-induces seizures in combined entorhinal cortex-hippocampal slices" (1994) Exp Brain Res 101, pp. 44-52, May 9, 1994.
Weiss, et al., "Quenching: inhibition of development and expression of amygdala kindled seizures with low frequency stimulation" (1995) Neuroreport 6, pp. 2171-2176, Nov. 1995.
Wieraszko, "Amplification of evoked potentials recorded from mouse hippocampal slices by very low repetition rate pulsed magnetic fields" (2004) Bioelectromagnetics 25, pp. 537-544, final form accepted Apr. 20, 2004.
Windels, et al., "Influence of the frequency parameter on extracellular glutamate and gamma-aminobutyric acid in substantia nigra and globus pallidus during electrical stimulation of subthalamic nucleus in rats" (2003) J Neurosci Res 72, pp. 259-267, Dec. 17, 2002.
Yamamoto, et al., "New method of deep brain stimulation therapy with two electrodes implanted in parallel and side by side" (2001) J Neurosurg 95, pp. 1075-1078, Dec. 2001.
Yearwood et al., "A prospective comparison of Spinal cord stimulation (SCS) Using Dorsal Column Stimulation (DCS), Intrapsinal Nerve Root Stimulation (INRS), and varying pulse Width in the Treatment of Chronic Low Back Pain" Digital Abstract presented at CNS 56th Annual Meeting, Chicago 2006, Jul. 10, 2006, 7 pgs.
Prosecution History from U.S. Appl. No. 16/055,787, dated Aug. 6, 2018 through Jul. 31, 2020, 95 pp.
De Leo et al., "The tetrapartite synapse: Path to CNS sensitization and chronic pain," Pain, ElSevier, Feb. 21, 2006, 5 pp.
Jang et al., "High frequency electrical stimulation promotes expression of extracellular matrix proteins from human astrocytes," Jul. 2, 2019, 7 pp.
Johanek et al., "The effects of modulating stimulation parameters of spinal cord stimulation (SCS) and glial activity in animals with neuropathic pain," Journal of Pain, Apr. 2011, 10 pp.
Roitbak et al., "Depolarization of cortical glial cells in Response to Electrical stimulation of the Cortical Surface," Neuroscience, vol. 6, No. 12, 1981, 9 pp. (Applicant points out, in accordance with MPEP 609.04(a), that the year of publication, 1981 is sufficiently earlier than the effective U.S. filing date, so that the particular month of publication is not in issue.).
Tilley et al., "Spinal Cord Stimulation Modulates Gene Expression in the Spinal Cord of an Animal Model of Peripheral Nerve Injury," Regional Anesthesia and Pain Medicine, vol. 41, Nov. 6, Nov.-Dec. 2016, 7 pp.
Vallejo et al., "Effects of Phase Polarity and Charge Balance Spinal Cord Stimulation on Behavior and Gene Expression in a Rat Model of Neuropathic Pain," Neuromodulation: Technology at the Neural Interface, Wiley OnlineLibrary, accepted Apr. 3, 2019, 10 pp.
Vallejo et al., "Genomics of the Effect of Spinal Cord Stimulation on an Animal Model of Neuropathic Pain," Neuromodulation: Technology at the Neural Interface, Wiley OnlineLibrary, May 11, 2016, 11 pp.
Vallejo et al., The Role of Glia and the Immune System in the Development and Maintenance of Neuropathic Pain, Review Article, Pain Practice, vol. 10, Issue 3, accepted Jan. 2010, 18 pp.
Milligan et al., "Pathological and protective roles of glia in chronic pain," vol. 10, Nature Reviews, Jan. 2009, 15 pp.
Gravius et al., Selective L4 Dorsal Root Ganglion Stimulation Evokes Pain Relief and Changes of Inflammatory Markers: Part I Profiling of Saliva and Serum Molecular Patterns, Neuromodulation: Technology at the Neural Interface, Aug. 15, 2018, 9 pp.
Guthrie et al., "ATP Released from Astrocytes Mediates Glial Calcium Waves," The Journal of Neuroscience, Jan. 15, 1999, 19(2), pp. 520-528, Jan. 15, 1999.
Prosecution History from U.S. Appl. No. 17/121,425, dated Jan. 22, 2021, through Mar. 24, 2021, 13 pp.
U.S. Appl. No. 16/901,202, filed Jun. 15, 2020, naming inventor Michael John, Sasha.
U.S. Appl. No. 16/901,206, filed Jun. 15, 2020, naming inventor Michael John, Sasha.
U.S. Appl. No. 17/007,563, filed Aug. 31, 2020, naming inventor Michael John, Sasha.
U.S. Appl. No. 17/007,570, filed Aug. 31, 2020, naming inventor Michael John, Sasha.
U.S. Appl. No. 17/060,610, filed Oct. 1, 2020, naming inventor Michael John, Sasha.
U.S. Appl. No. 17/121,425, filed Dec. 14. 2020, by Vallejo et al.
AU Application No. 2016235457 Examination Report dated Dec. 17, 2019, 4 pages.
EP Application No. 16769480.1 Extended EP Search Report dated Jan. 30, 2019, 10 pages.
EP Application No. 16769480.1 Office Action dated Nov. 7, 2019, 5 pages.
EP Application No. 17842263.0 Extended EP Search Report dated Feb. 20, 2020, 9 pages.
Hailong Liu et al., "Modulation of Axonal Excitability by High-Frequency Biphasic Elecliical Current," IEEE Transactions on Biomedical Engineering, vol. 56, No. 9, Sep. 1, 2009, pp. 2167-2176.
International Application No. PCT/US16/23365 International Search Report dated Aug. 12, 2016, 5 pages.
International Application No. PCT/US17/47798 International Search Report and Written Opinion dated Jan. 18, 2018, 9 pages.
International Application No. PCT/US2016/023365 International Preliminary Report on Patentability dated Aug. 12, 2016, 13 pages.
Li et al., "CaBP1, a neuronal Ca2+ sensor protein, inhibits inositol trisphosphatae receptors by claimping intersubunit interactions," PNAS, 2013, 110(21): 8507-8512.
Zhang, et al. Neuronal calcium-binding proteins 1/2 localize to dorsal root ganglia and excitatory spinal neurons and are regulated by nerve injury. Pro Natl Acad Sci USA Mar. 25, 2014; 111(12):E1149-58.
Examiner's Report and Search Report from counterpart Canadian Application No. 2983582 dated Nov. 15, 2022, 6 pp.

METHOD AND APPARATUS FOR MULTI MODAL ELECTRICAL MODULATION OF PAIN

CROSS REFERENCE TO RELATED PARAGRAPHS

This application is a continuation of U.S. application Ser. No. 16/055,787 filed Aug. 6, 2018, which is a continuation-in-part of Ser. No. 15/075,550 filed Mar. 21, 2016, [now U.S. Pat. No. 10,039,930], which claims priority to and benefit of U. S. Provisional Application Ser. No. 62/135,999, filed Mar. 20, 2015, entitled METHOD AND APPARATUS FOR BIMODAL MODULATION IN PAIN MANAGEMENT, and U.S. Provisional Application Ser. No. 62/196,030, filed Jul. 23, 2015, entitled METHOD AND APPARATUS FOR BIMODAL ELECTRICAL MODULATION IN PAIN, the contents of which are incorporated by reference herein in their entirety for all purposes.

FIELD

This disclosure relates to systems and methods for providing multimodal stimulation of neural structures, and, more specifically, for managing pain with either multiple signals or a single signal having modulated characteristics.

BACKGROUND

The term Spinal Cord Stimulation (SCS) is used to describe an advanced management therapy for chronic pain in which a varying electric field is applied to the Dorsal section of the spinal Cord (DC) via an electrode array (or electrode arrays) implanted in the epidural space. Conventional SCS also called tonic, traditionally utilizes an electric field varying between 40-250 Hz that is directed to a targeted pain location by overlaying it with a perceived tingling sensation, known as paresthesia, created by the stimulating electric field. This therapy has been clinically utilized for about half a century. The principle mode of action is based on the Gate Control Theory formulated by Melzack and Wall, although a full understanding of the mechanism has yet to be elucidated. The concept behind tonic SCS is that the paresthesia induced by the applied varying electric field masks, or "closes the gates to", pain signals travelling to the brain, however, the relationship between frequency, waveform shape, amplitude and pulse width and the mechanism by which SCS provides an analgesic effect is not fully understood.

SUMMARY

Disclosed herein are apparatus and methods for managing pain in a patient by using multimodal stimulation of neural structures, with either multiple signals or a single signal having modulated characteristics. Multimodal modulation for pain management, in accordance with the disclosure, contemplates the use of multiple separate varying or oscillating electromagnetic fields which are independently applied via an array of electrodes (referred as contacts or leads) to a particular neural structure using a variety of temporal and amplitude characteristics, to modulate glial and neuronal interactions as the mechanism for relieving chronic pain. Specifically, disclosed is an apparatus and method for modulating the expression of genes involved in diverse pathways including inflammatory/immune system mediators, ion channels and neurotransmitters, in both the Spinal Cord (SC) and Dorsal Root Ganglion (DRG). In one embodiment, such expression modulation is caused by spinal cord stimulation or peripheral nerve stimulation. In one embodiment, the amplitudes and frequencies of the signal or signals used to create the multimodal stimulation of neural structures may be optimized for improved pain relief and minimal power usage in an implantable multimodal signal generator, as described herein.

According to one aspect, the present disclosure provides a method for stimulating/modulating the interaction between glial cells and neurons of a subject comprising: A) exposing glial cells and neurons of the subject to a first stimulus; and B) simultaneously exposing the glial cells and neurons of the subject to a second stimulus; wherein the first stimulus and the second stimulus have at least one uncommon parameter therebetween. In one embodiment, the first stimulus and the second stimulus comprise electrical signals. In another embodiment, the electrical signals have different values for any of their respective frequency, amplitude, phase or waveform shape.

According to another aspect, the present disclosure provides a method for stimulating and modulating the interaction between glial cells and neurons of a subject comprising: A) exposing glial cells and neurons of the subject to a first stimulus; and B) exposing the glial cells and neurons of the subject to a second stimulus; wherein the first stimulus and the second stimulus have a common parameter therebetween. In one embodiment, the first stimulus comprises a first varying electric field and the second stimulus comprises a second varying electric field. In another embodiment, the first varying electric field and the second varying electric field are provided by a composite electrical signal. In still another embodiment, the composite electrical signal may be any of an amplitude modulated, frequency modulated, summation, or pulse width modulated signal.

According to another aspect, the present disclosure provides a method for stimulating and modulating the interaction between glial cells and neurons of a subject comprising: A) exposing glial cells and neurons of the subject to a first stimulus; and B) simultaneously exposing the glial cells and neurons of the subject to a second stimulus; wherein the first stimulus and the second stimulus have a common parameter therebetween. In one embodiment, the first stimulus and the second stimulus comprise electrical signals having substantially the same of any of amplitudes, frequencies, phases, or waveform shapes.

According to yet another aspect, the present disclosure provides a method for stimulating and modulating the interaction between glial cells and neurons of a subject comprising: A) providing lead arrays having a plurality of electrode contacts electrically coupleable to an electrical signal source; B) electrically coupling a first subgroup of the plurality of electrode contacts to a first electrical signal source; C) electrically coupling a second subgroup of the plurality of electrode contacts to a second electrical signal source; D) exposing glial cells and neurons of the subject to the first electrical signal from the first subgroup of electrode contacts; and E) simultaneously exposing the glial cells and neurons of the subject to the second electrical signal from the second subgroup of electrode contacts.

According to still another aspect, the present disclosure provides a method for managing pain in a subject comprising: A) activating glial cells by regulating any of genes for calcium binding proteins, cytokines, cell adhesion or specific immune response proteins without the administration of a pharmacological compound to the subject. In one embodiment, activating the glial cells comprises exposing the glial cells to a first stimulus which may be a varying electromagnetic field. In another embodiment, activating the glial cells comprises exposing the glial cells to a second stimulus, substantially simultaneously with the first stimulus, wherein the second stimulus comprises a second varying electromagnetic field. In still another embodiment, the first and second varying electromagnetic fields have one of different frequency, amplitude, phase, or harmonic content.

According to yet another aspect, the present disclosure provides a method for managing pain in a subject comprising: A) lowering a threshold for depolarization of nerve fibers in the subject with a first varying electromagnetic field; and B) simultaneously activating glial cells with a second varying electromagnetic field; without the administration of a pharmacological compound to the subject. In one embodiment, the first varying electromagnetic field and the second varying electromagnetic field have any of different respective frequencies, amplitudes, phases or harmonic content. In another embodiment, the first and second varying electromagnetic fields may be provided by either a single electrical signal or by two different electrical signals.

According to still another aspect, a method for managing pain in a subject comprises: A) lowering a threshold for depolarization of nerve fibers in the subject with a first varying electromagnetic field for a first period of time; and B) simultaneously modulating glial cell activity with a second varying electromagnetic field during a second period of time not identical to the first period of time causing down-regulation of calcium binding protein (cabp1) within the modulated glial cell.

According to yet another aspect, a method for managing pain in a subject comprises: A) lowering a threshold for depolarization of nerve fibers in the subject with a first varying electromagnetic field for a first period of time; and B) simultaneously modulating glial cell activity with a second varying electromagnetic field during a second period of time not identical to the first period of time causing up-regulation of any of Toll-like receptor 2 (tlr2), Chemokine cxcl16, and Glial maturation factor (Gmfg) within the modulated glial cells.

According to still another aspect, a method for managing pain in a subject comprises: A) lowering a threshold for depolarization of nerve fibers in the subject with a first varying electromagnetic field for a first period of time; and B) simultaneously modulating glial cell activity with a second varying electromagnetic field during a second period of time not identical to the first period of time; wherein the varying electromagnetic fields change synaptic plasticity of neurons and glial cells within the neural structures.

According to yet another aspect, a method for managing pain in a subject comprises: A) lowering a threshold for depolarization of nerve fibers in the subject with a first varying electromagnetic field for a first period of time; and B) simultaneously modulating glial cell activity with a second varying electromagnetic field during a second period of time not identical to the first period of time; wherein the first varying electromagnetic field is provided by an electric signal having an amplitude set to a value corresponding to a percentage of a Priming Perception Threshold (PPT) of the subject, and wherein a second varying electromagnetic field is provided by an electric signal having an amplitude set to a value corresponding to a percentage of the paresthesia threshold (PT).

In one embodiment of multimodal modulation therapy, the priming signal may be monophasic, or biphasic, in which the polarity of the first phase of the biphasic priming signal may be either cathodic or anodic. With this embodiment, the tonic signal may have waveform characteristics that are different from those of the priming signal. The tonic signal may be either monophasic, or biphasic, with the polarity of the first phase of the biphasic tonic signal being either cathodic or anodic. Biphasic stimulation increases the amount of genes related to glial activation (tlr2 and cxcl16) relative to anodic and cathodic stimulation while monophasic cathodic stimulation causes the release of glutamate from astrocytes. Biphasic stimulation increases the amount of cabp1 relative to monophasic stimulation (cathodic or anodic). Monophasic stimulation (cathodic or anodic) and biphasic stimulation affect similarly the amount of the immune-related gene cd 68 and the expression of the gene coding for the opioid receptor oprm1.

According to one aspect, the present disclosure provides a method for stimulating/modulating the interaction between glial cells and neurons of a subject comprising: A) exposing glial cells and neurons of the subject to a first stimulus; and B) simultaneously exposing the glial cells and neurons of the subject to a second stimulus; wherein the first stimulus and the second stimulus have different respective phase polarities. In one embodiment, the first stimulus and the second stimulus comprise electrical signals. In another embodiment, the electrical signals have different values for any of their respective frequency, amplitude, waveform shape, or width in the case of rectangular waveforms.

According to another aspect, the present disclosure provides a method for stimulating and modulating the interaction between glial cells and neurons of a subject comprising: A) providing lead arrays having a plurality of electrode contacts electrically coupleable to an electrical signal source; B) electrically coupling a first subgroup of the plurality of electrode contacts to a first electrical signal source; C) electrically coupling a second subgroup of the plurality of electrode contacts to a second electrical signal source; D) exposing glial cells and neurons of the subject to the first electrical signal from the first subgroup of electrode contacts; and E) simultaneously exposing the glial cells and neurons of the subject to the second electrical signal from the second subgroup of electrode contacts wherein the first electrical signal and the second electrical signal have different respective phase characteristics.

According to still another aspect, the present disclosure provides a method for managing pain in a subject comprising: A) activating glial cells during a first time period by regulating any of genes for calcium binding proteins, cytokines, cell adhesion or specific immune response proteins; and B) administering a pharmacological substance to the subject during a second time period not identical to the first time. In one embodiment, such a pharmacological substance suitable for use with the disclosed method may comprise a metabotropic or ionotropic glutamate receptor antagonist such as (S)-4-carboxyphenylglycine (CPG), (RS)-a-methyl-4-carboxyphenylglycine (MCPG), or kynurenic acid (KYA). In another embodiment, a suitable pharmacological substance may comprise a potassium channel antagonist, such as 4-aminopyridine (4AP), or an alpha-2 adrenergic receptor agonist, such as clonidine, or a calcium channel agonist such as the w-conotoxin MVllC. Such pharmacological substances can help to activate or deactivate glial cells by modulating the release of glutamate, potassium or calcium ions in or out the glial cell. In one embodiment, activating the glial cells comprises exposing the glial cells to a first stimulus which may be a varying electromagnetic field. In another embodiment, activating the glial cells comprises exposing the glial cells to a second stimulus, substantially simultaneously with the first stimulus, wherein the second stimulus comprises a second varying electromagnetic field. In still another embodiment, the first and second varying electromagnetic fields have one of different frequency, amplitude, phase polarity, relative phase, harmonic content, or width for rectangular waveforms.

According to yet another aspect, the present disclosure provides a method for managing pain in a subject comprising: A) lowering a threshold for depolarization of nerve fibers in the subject with a first varying electromagnetic field; and B) simultaneously modulating glial cell activity with a second varying electromagnetic field; wherein the electromagnetic fields control the balance of glutamate and glutamine in a calcium dependent manner within the modulated glial cells. In one embodiment, the first varying electromagnetic field and the second varying electromagnetic field have any of different respective frequencies, amplitudes, phases, harmonic content, or width for rectangular waveforms. In another embodiment, the first and second varying electromagnetic fields may be provided by either a single electrical signal or by two different electrical signals.

According to still another aspect, a method for managing pain in a subject comprises: A) lowering a threshold for depolarization of nerve fibers in the subject with a first varying electromagnetic field for a first period of time; and B) simultaneously modulating glial cell activity with a second varying electromagnetic field during a second period of time not identical to the first period of time wherein the characteristics of the varying magnetic fields control any of glial depolarization, release or uptake of ions, and release of glial transmitters by the glial cells.

According to yet another aspect, a method for managing pain in a subject comprises: A) lowering a threshold for depolarization of nerve fibers in the subject with a first varying electromagnetic field for a first period of time; and B) simultaneously modulating glial cell activity with a second varying electromagnetic field during a second period of time not identical to the first period of time, wherein the first varying electromagnetic field is provided by an electric signal having a first phase polarity portion which stimulates glial cells to release glutamate, and wherein a second varying electromagnetic field is provided by the electric signal having a second phase polarity portion which stimulates release of glutamate from astrocytes within the glial cells.

According to still another aspect, a method for managing pain in a subject comprises: A) lowering a threshold for depolarization of nerve fibers in the subject with a first varying electromagnetic field for a first period of time; and B) simultaneously modulating glial cell activity with a second varying electromagnetic field during a second period of time not identical to the first period of time; wherein the manipulation of any of the frequency, amplitude, waveform, width and phase of electrical signal generating the first and second varying electromagnetic fields modulates the behavior of glial cells and interaction thereof with neurons at the synaptic level.

According to yet another aspect, a method for managing pain in a subject comprises: A) modulating glial cells in a subject with a monophasic electromagnetic signal having cathodic polarity thereof selected to stimulate glial cells to release glutamate; and B) modulating glial cells in a subject with a monophasic electromagnetic signal having anodic polarity thereof selected to stimulate glial cells to inhibit the release of glutamate.

According to still another aspect, a method for managing pain in a subject comprises: A) modulating glial cells with an asymmetric biphasic electromagnetic signal having variable duration of the anodic phase thereof selected to modulate the amount of glutamate released therefrom; and B) modulating glial cells with an asymmetric biphasic electromagnetic signal having variable duration of the cathodic phase thereof selected to modulate the amount of glutamate released therefrom.

According to yet another aspect, a method for managing pain in a subject comprises: A) modulating glial cells with an asymmetric biphasic electromagnetic signal having variable duration of the cathodic and anodic phases thereof selected to modulate the amount of glutamate released therefrom, wherein the electromagnetic fields control the balance of glutamate and glutamine in a calcium dependent manner within the modulated glial cells.

According to yet another aspect, a system is provided comprising a signal generation module and one or more leads. The leads are configured for exposing glial cells and neurons simultaneously to a first electromagnetic stimulus and a second electromagnetic stimulus. The signal generation module is configured for having an operating mode for providing a first and a second electric signal having at least one common parameter therebetween or at least one uncommon parameter therebetween to the one or more leads.

Also disclosed herein is an apparatus comprising a signal generation module that is configured for electrically coupling with one or more leads. Coupling of the apparatus with one or more leads may provide the system.

Optionally, the signal generation module comprises at least a first and a second electric signal source or terminal and the one or more leads comprise at least a first and a second subgroup of electrodes. The first subgroup of electrodes can be electrically coupled to the first electric signal source and/or terminal and the second subgroup of electrodes can be electrically coupled to the second electric signal source and/or terminal.

Optionally, the signal generation module is configured for having an operating mode for providing at least first and second electric signals corresponding to the first and second electromagnetic stimulus as described herein. Optionally, the first and second electric signals have a different frequency.

Optionally, the signal generation module is configured for having an operating mode for providing electric signals to the electrodes corresponding to the electromagnetic stimulus of any of the methods described herein.

Optionally, the signal generation module is configured for having an operating mode for providing a Priming signal to the first subgroup of electrodes and, e.g. simultaneously, a Tonic signal to the second subgroup of electrodes, e.g. as described herein. The signal generation module can be configured for having an operating mode for providing a first electric signal having a frequency between 200 Hz to 1,500 Hz to the first subgroup of electrodes, and a second electric signal having a frequency lower than the first electric signal, such as between 20 Hz and 150 Hz, to the second subgroup of electrodes. The signal generation module may be configured for having an operating mode for providing a priming signal and a tonic signal with a ration of the frequency of the priming signal to the tonic signal in the range of 20:1 to 40:1.

Optionally, the signal generation module is arranged for generating a composite electric signal. The composite electric signal can be a summed signal of the first and second electric signals. Optionally, the signal generation module is arranged for generating a multimodal signal, such as a frequency-modulated signal or an amplitude modulated signal. The composite signal and/or the multimodal signal can be provided to the one or more leads.

Optionally, the signal generation module can be configured for having an operating mode for providing a first electric signal having a frequency to the first subgroup of electrodes, and a second electric signal having the same frequency to the second subgroup of electrodes. The frequency can be between 500 Hz and 1,500 Hz. Other parameters of the first and second electric signals may be different, such as the pulse width and/or amplitude. The first electric signal can be fired synchronously, i.e. simultaneously, with the second electric field, or asynchronously, e.g. with a given time delay, relative to the first electric signal.

As used herein, a signal generation module that is configured for having an operating mode may comprise a memory module containing instructions defining at least an operating mode as described, wherein the operating mode is optionally a user-selectable operating mode and the memory module optionally comprises instructions for additional operating modes. In certain embodiments the signal generation module is configured for delivering electrical signals to one or more leads as specified.

Optionally, the signal generation module comprises two or more electric signal sources, such as signal generators, that are independently controllable, and are configured for delivering electric signals with parameters that can be set separately for each of the electric signal sources.

Optionally, the apparatus is a non-implantable, e.g. trialing, system comprising a signal generation module comprising at least two signal generators configured for delivering electric signals with parameters that can be set separately for each of the signal generators, for example a Priming signal and a Tonic signal.

Optionally, an implantable multimodal generator is provided, that is adapted for electrically coupling with one or more leads, or optionally is coupled with one or more leads. The implantable multimodal generator comprises generator circuitry and a housing. The housing can hermetically seal the generator circuitry and can be made of a durable biocompatible material. The generator has an output interface for establishing electrical connection with electrodes implemented in one or more leads, e.g. a first and second terminal for electrically coupling to a first and second subgroup of electrodes implemented on one or more leads.

Optionally the implantable multimodal generator comprises two or more signal generators and timer electronic circuitry that can slave one of the signal generators to another signal generator, such that a delay can be produced between signals generated from the at least two signal generators.

According to another aspect of the disclosure, an electromagnetic stimulation device is provided including an output unit for connection to at least one electrode array, or a plurality of arrays of electrodes, and a signal generator, wherein the stimulation device is arranged for providing a multimodal stimulation signal to at least one electrode array, or a plurality of arrays of electrodes via the output unit. The multimodal stimulation signal can be an electromagnetic signal. At least one electrode array is configured for exposing glial cells and neurons to the multimodal stimulation signal. The electromagnetic stimulation device can be a pain treatment device.

Optionally, the electromagnetic stimulation device may have an output unit that includes a first output for connection to a first lead and a second output for connection to a second lead. The first lead can include a first array of electrodes. The second lead can include a second array of electrodes.

Optionally, the signal generator is arranged for providing a first electric signal to the first output and a second electric signal to the second output. The first electric signal and the second electric signal can differ in a parameter such as amplitude, frequency, phase, phase polarity, waveform shape, and width. The first electric signal and the second electric signal may correspond in a parameter such as amplitude, frequency, phase, phase polarity, waveform shape, and width. The second electric signal can be a tonic stimulation signal, and the first electric signal can have a frequency higher than the frequency of the tonic stimulation signal.

Optionally, the signal generator is arranged for generating a multimodal electric signal, such as a frequency modulated signal or an amplitude modulated signal. The multimodal electric signal can be provided to at least one electrode.

According to another aspect of the disclosure, a method for operating a signal generation module is provided. The method includes connecting the signal generation module to one or more leads. The leads can already have been provided to a body of a subject. The method includes generating, using the signal generation module, a first oscillating electromagnetic field at least one of the one or more leads and generating, using the signal generation module, a second oscillating electromagnetic field at least one of the one or more leads. The first oscillating electromagnetic field and the second oscillating electromagnetic field can have at least one uncommon parameter therebetween.

According to another aspect of the disclosure, an electrically conducting material is provided, such as a metal, e.g. in the form of an electrode, for use in administering an electromagnetic stimulus into a subject for the treatment of pain. The electromagnetic stimulus can include a first electromagnetic stimulus and a second electromagnetic stimulus. The first stimulus and the second stimulus may have at least one uncommon parameter therebetween. The first stimulus and the second stimulus can be signals, or a composite signal, or multimodal signal as described herein.

Optionally, the first stimulus is a Priming signal and the second stimulus is a Tonic signal. The first stimulus can have a frequency between 200 Hz to 1,500 Hz. The second stimulus can have a frequency lower than the first stimulus, such as between 20 Hz and 150 Hz. The frequency of the first stimulus and the frequency of the second stimulus can have a ratio in the range of 20:1 to 40:1.

According to another aspect of the disclosure, an electromagnetic stimulation system comprises a memory for storing a plurality of multimodal signal parameter programs; a selection device for selecting one of the plurality of multimodal signal parameter programs; a multimodal signal generator controllable by a selected of the plurality of multimodal signal parameter programs; and an output unit for connection to at least one electrode; wherein the stimulation device is configured to provide a multimodal stimulation signal generated by the multimodal signal generator in accordance with a selected of the multimodal signal parameter programs to the at least one electrode via the output unit. The system may further comprise an enclosure of biocompatible material surrounding the multimodal signal generator and output unit. In one embodiment, the multimodal signal generator generates a first and second electric signals on in an operational mode thereof. In one embodiment, the system may be combined with at least one electrode comprising at least a first and a second subgroup of electrodes, and wherein the first subgroup of electrodes is electrically coupled to the first electric signal and the second subgroup of electrodes is electrically coupled to the second electric signal.

It will be appreciated that any of the aspects, features and options described in view of the methods apply equally to the system, signal generation module and stimulation device. It will be understood that any one or more of the above aspects, features and options as described herein can be combined.

BRIEF DESCRIPTION OF DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

Figure 1:
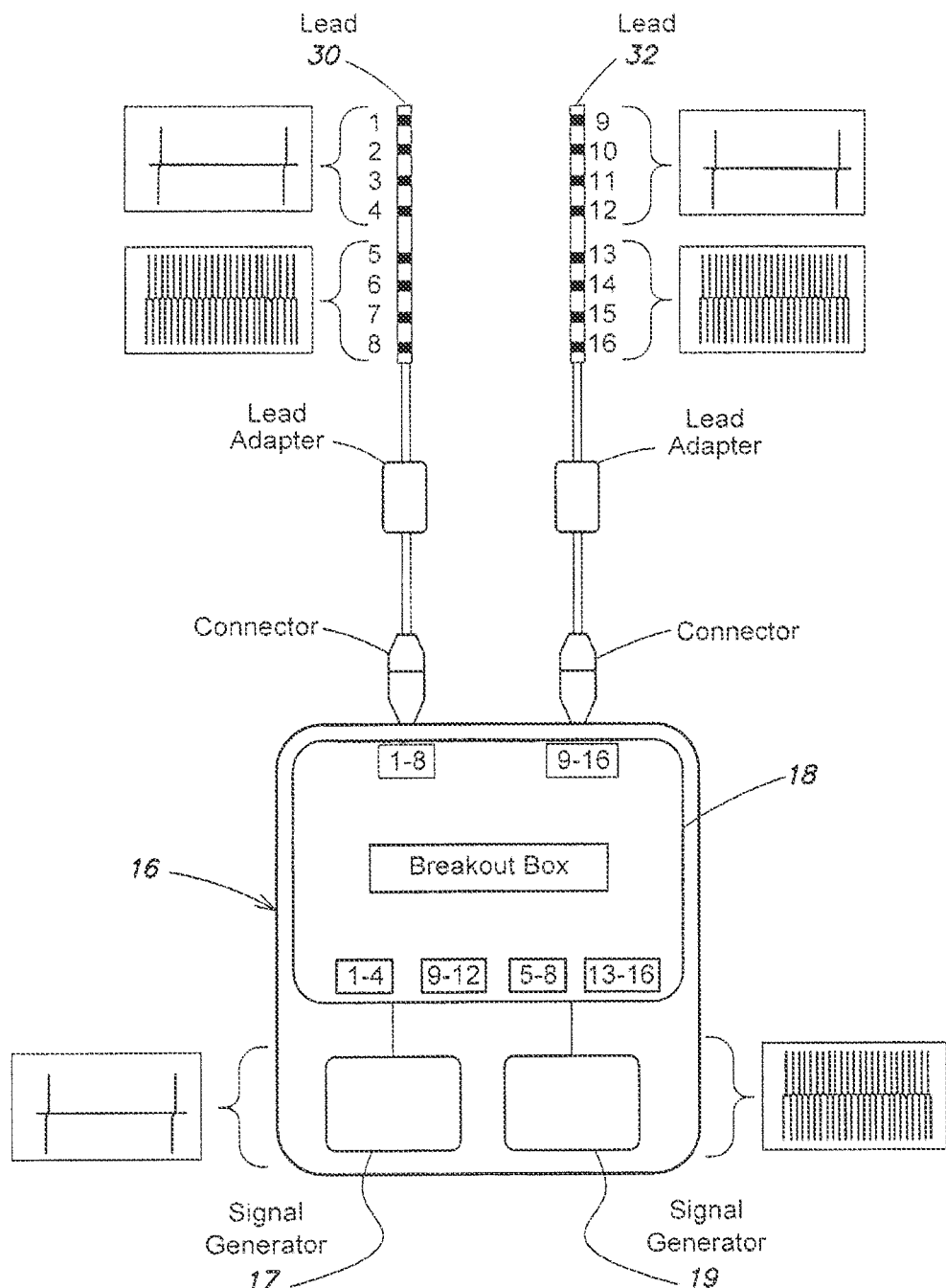
FIG. 1 is a schematic diagram illustrating an apparatus for pain management in accordance with an embodiment of the present disclosure.

The present disclosure will be more completely understood through the following description, which should be read in conjunction with the drawings. In this description, like numbers refer to similar elements within various embodiments of the present disclosure. The skilled artisan will readily appreciate that the methods, apparatus and systems described herein are merely exemplary and that variations can be made without departing from the spirit and scope of the disclosure.

The oscillatory electromagnetic fields applied to neural structures induce changes in synaptic plasticity upon modulation of two different cell populations: Neurons and glial cells. This is concurrent with the well-known effects on neurons such as action potential generation or blockade by the stimulation of mechanosensitive fibers to mask (or close the gate to) nociceptive signals travelling to the brain. As such, paresthesia is a byproduct and not a pre-requisite to attain pain relief during conventional electrical stimulation. In addition, glial cells are immunocompetent cells that constitute the most common cell population in the nervous system and play a fundamental role in the development and maintenance of chronic neuropathic pain. Glial cells are responsible for monitoring the status of the nervous system by using constant chemical communication with neurons and other glial cells. Microglia are the glial cells in charge of monitoring the brain and spinal cord. Following a nerve (or brain) injury, these cells become activated and respond to any stimulus that is considered a threat to Central Nervous System (CNS) homeostasis. This activation involves morphological changes in the microglia accompanied by changes in chemotaxis and phagocytic activity, as well as the release of chemokines and cytokines that induce a response from the immune system. It has been shown that microglia are the CNS immediate responders to injury. Injury also triggers the activation of astrocytes, glial cells that monitor the synaptic clefts and thus are involved in synaptic plasticity via the regulation of neuro and glial transmitter molecules and involvement of immune cells for synaptic pruning. Astrocyte activation and regulation is sustained for longer time and thus it can be hypothesized that astrocytes play an important role in changes affecting synaptic plasticity in chronic pain. There is experimental evidence that supports this hypothesis. It is worth noting that at the Peripheral Nervous System (PNS), oligodendrocytes, Schwann cells and satellite glial cells, similar to astroglia, play similar roles.

Calcium ions and phosphorylating processes mediated by ATP play an important role in glial response to injury. Electrical impulses induce changes in the concentration of calcium ions in the astrocytes, which propagates between astrocytes via calcium waves. This, in turn, signals the release of transmitters such as glutamate, adenosine and ATP, even after sodium channel blockade, which modulates both neuronal excitability and synaptic transmission. The presence of an external oscillatory electrical field then provides a stimulus for glial cells to affect synapses that have been negatively affected by injury. The electrical field provides a priming response that moves the function of the synapse towards a normal state.

It is possible to electrically stimulate glial cells as their response (glial depolarization, release/uptake on ions, release of glial transmitters) depends on the specific parameters such as amplitude, frequency, phase polarity, waveform shape, and width (in the case of rectangular waveforms) of the stimulation. For example, the release of glutamate from astrocytes may be modulated in proportion to the amount of anodic current administered during biphasic pulsed stimulation. Monophasic cathodic stimulation of hippocampal astrocytes promotes the release of glutamate. The introduction of an anodic component decreases the amount of glutamate released. Given that the glial cells and neurons respond differently to electrical fields, it is then possible to differentially modulate the response of these cell populations with distinctively different electrical parameters. This theory sets the mechanistic basis of multimodal stimulation. Subthreshold stimulation with an electromagnetic field set at an optimum frequency, amplitude, waveform, width and phase may modulate the behavior of glial cells and the way they interact with neurons at the synaptic level. Thus, multimodal modulation provides the ability to control the balance of glutamate and glutamine in a calcium dependent manner and the possibility of modulating such balance in the appropriate manner with electromagnetic fields.

Electromagnetic fields modulate the expression of genes and proteins, which are involved in many processes involving synaptic plasticity, neuroprotection, neurogenesis, inflammation. A full genome analysis of the ipsilateral DC and DRG obtained from an animal model of chronic neuropathic pain, in which SCS was applied continuously for 72 hours provided findings that were used to develop the multimodal methodologies described below. The results indicate that the analgesic effect may be induced at the molecular level in addition to, or independently of, the electric field blocking or masking nerve signaling. For example, SCS upregulates genes for calcium binding proteins (cabp), cytokines (tnf, il6, il1b, cxcl16, ifg), cell adhesion (itgb) and specific immune response proteins (cd68, tlr2) which are linked to glial activation. Modulation parameters, particularly the oscillation frequency and amplitude, may play an important role in the mode of action.

Multimodal Modulation Methodology

According to one aspect of the disclosure, a method for multimodal modulation, referred to as "prime" modulation utilizes electrode arrays, with some of the electrodes configured to deliver an electric field oscillating at a frequency higher than that typically used in tonic stimulation. The electrical field of this priming signal provides a persistent electrochemical potential that facilitates the stimulation of nerves by another field that is oscillating at a lower frequency. The priming signal lowers the threshold for depolarization of nerve fibers while simultaneously modulating glial activation. The priming signal also lowers the impedance of the stimulated tissue, which allows for better penetration of the electric field into the neural tissue. The frequent pulsing of the priming signal also contributes to a lower threshold for depolarization of nerve fibers via membrane integration of the electrical stimulus. Additionally, the priming signal contributes to neuronal desynchronization which is a mechanism that helps with the reestablishment of neuronal circuits that have been unnaturally synchronized to maintain a nociceptive input into the brain. In the disclosed prime multimodal modulation technique, a mechanism of depolarization is combined with amplitudes lower or slightly higher than the Paresthesia Threshold (PT), so the patient may or may not experience tingling even though tonic stimulation is being applied. A priming signal provides electrical stimulation at frequencies which will activate the molecular mechanisms that allow for resetting of the synaptic plasticity to a state closer to the one previous to central sensitization induced by injury, thus providing a mechanism for long lasting pain relief. The Priming Frequency (PF) may be set to any frequency below 1,500 Hz, but above the tonic frequency. In one embodiment, the PF may be set to any frequency between 200 Hz to 1,500 Hz. When a charged-balanced pulsed rectangular electrical signal, e.g. biphasic symmetric, biphasic asymmetric, capacitor coupled monophasic, is used, the Pulse Width (PW) may be set as low as 10 µs and as large as allowed by the priming frequency. For example, the maximum PW for a biphasic signal with equal PW per phase and a 20 µs interphase delay is 395 µs for PF=1,200 Hz or 980 µs for PF=500 Hz. Either a voltage or current controlled signal may be used, although a current controlled signal may be more desirable as such signal does not depend on temporal impedance variations in the tissue being stimulated. The amplitude of the priming field may be preferably set at a value below a Priming Perception Threshold (PPT), although setting it at or above the PPT is not excluded. The PPT may be found by slowly increasing the amplitude while feedback is obtained from the subject. Once the onset of perception is recorded, then the amplitude of the priming signal may be changed to a value which is a percentage of the PPT (% PPT). With an exemplary PF of 1500 Hz, the signal may be then set for a given time, e.g. 10-30 minutes, before an electric field set at a tonic frequency lower than the PF, e.g. 10 Hz to 1,499 Hz, is applied independently to other electrodes in the lead. In one embodiment, with an exemplary PF of 200 Hz, the tonic frequency may be in the range of approximately 10 Hz to 199 Hz, for example. In the prime mode of stimulation, the tonic frequency will be lower than the priming frequency but is not necessarily limited to a particular range of frequencies below the prime frequency. The Pulse Width (PW) of a charged-balance, e.g. a biphasic symmetric, biphasic asymmetric, or capacitor coupled monophasic, pulsed signal can be as low as 10 µs and as large as allowed by the set tonic frequency. This PW is set to provide a low duty cycle, which will minimize potential field interference between this field and the priming field, especially in electrode arrangements that are spatially proximal. Spatial interference of the fields can also be reduced by including an electronic component in the circuitry that can time the delivery of the tonic signal relative to the priming signal. For example, the priming and tonic signals can be delivered synchronously or asynchronously with a delay therebetween. The signal generation and delivery circuitry may also allow for modifying the duty cycles of pulsed width signals and various schemes in which the time of initial priming can be varied, as well as the times in which the priming signal is on or off relative to the time when tonic signal is delivered. The amplitude of the tonic electric field, which could be either voltage or current controlled, may be set above, below or at the paresthesia or perception threshold (PT). PT may be obtained by increasing the amplitude of the signal while getting feedback from the patient. The tonic amplitude may then be set to a value corresponding to a percentage of the PT (% PT). In the prime multimodal modulation methods described herein both the priming signal and the tonic signal may be below 1,500 Hz, in one embodiment. In another embodiment, the tonic signal may be below 500 Hz. In still another embodiment, the tonic signal may be below 100 Hz. In one embodiment, the ratio of priming signal frequency to tonic signal frequency may be in the range of 20:1 to 40:1, depending on the specific values of the frequencies chosen.

Figure 18:
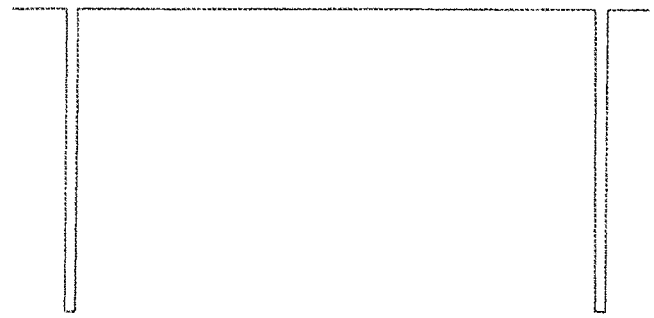
FIG. 18 illustrates conceptually a trace representing a signal having a monophasic cathodic rectangular waveform followed by a interphase delay for passive charge balance that may be used in accordance with an embodiment of the present disclosure.
Figure 19:
FIG. 19 illustrates conceptually a trace representing a signal having a monophasic anodic rectangular waveform followed by a interphase delay for passive charge balance that may be used in accordance with an embodiment of the present disclosure.
Figure 20:
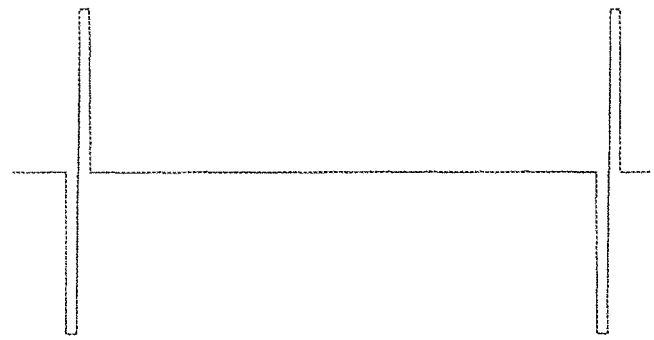
FIG. 20 illustrates conceptually a trace representing a signal having a biphasic symmetric rectangular waveform in which the first phase is cathodic that may be used in accordance with an embodiment of the present disclosure.
Figure 21:
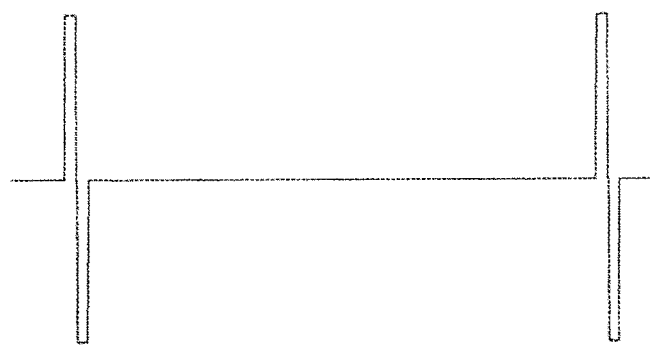
FIG. 21 illustrates conceptually a trace representing a signal having a biphasic symmetric rectangular waveform in which the first phase is anodic that may be used in accordance with an embodiment of the present disclosure.
Figure 22:
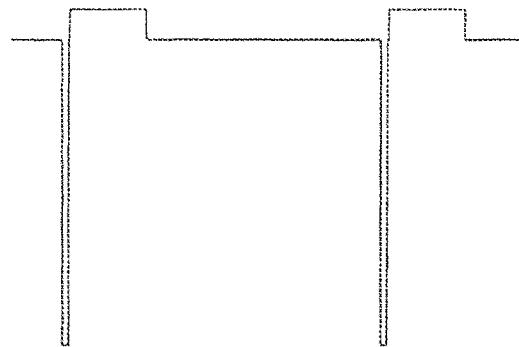
FIG. 22 illustrates conceptually a trace representing a signal having a biphasic asymmetric rectangular waveform in which the first phase is cathodic and the second, anodic phase, is of smaller amplitude and longer width in accordance with an embodiment of the present disclosure.
Figure 23:
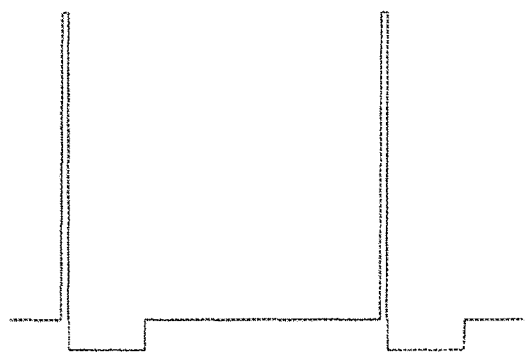
FIG. 23 illustrates conceptually a trace representing a signal having a biphasic asymmetric rectangular waveform in which the first phase is anodic and the second, cathodic phase, is of smaller amplitude and longer width in accordance with an embodiment of the present disclosure.
Figure 24:
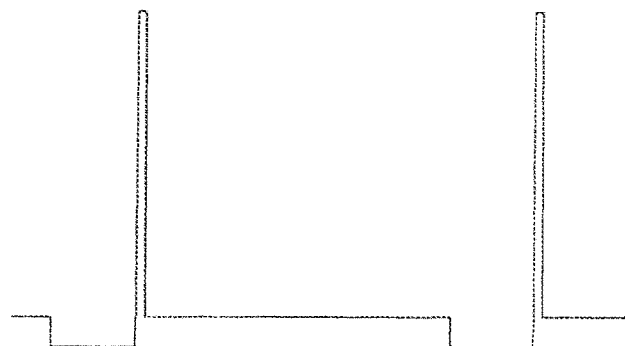
FIG. 24 illustrates conceptually a trace representing a signal having a biphasic asymmetric rectangular waveform in which the first phase is cathodic and the second, anodic phase, is of larger amplitude and shorter width in accordance with an embodiment of the present disclosure.
Figure 25:
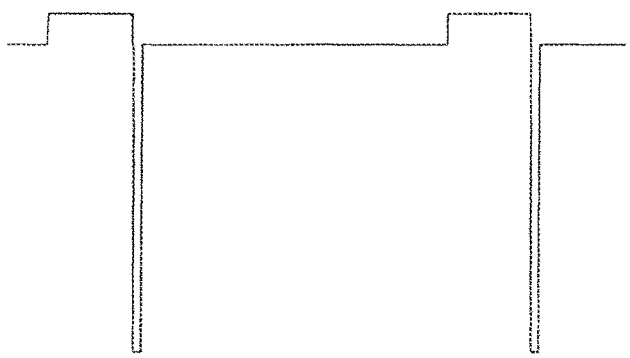
FIG. 25 illustrates conceptually a trace representing a signal having a biphasic asymmetric rectangular waveform in which the first phase is anodic and the second, cathodic phase, is of larger amplitude and shorter width in accordance with an embodiment of the present disclosure.
Figure 26:
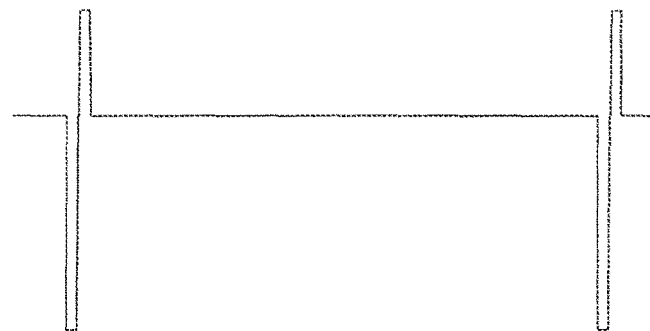
FIG. 26 illustrates conceptually a trace representing a signal having a biphasic asymmetric rectangular waveform in which the first phase is cathodic and the second, anodic phase, is of the same width and smaller amplitude.
Figure 27:
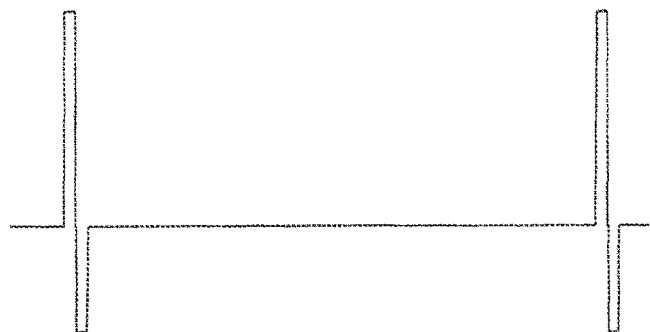
FIG. 27 illustrates conceptually a trace representing a signal having a biphasic asymmetric rectangular waveform in which the first phase is anodic and the second, cathodic phase, is of the same width and smaller amplitude in accordance with an embodiment of the present disclosure.
Figure 28:
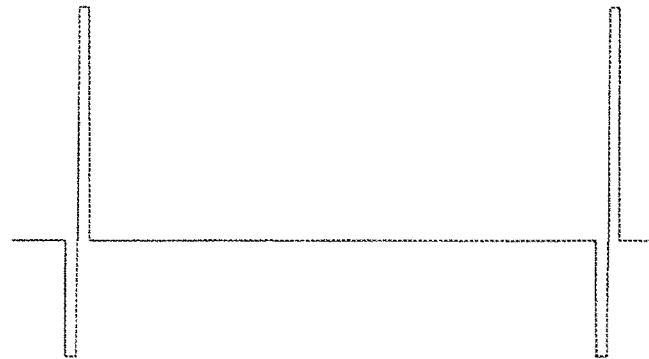
FIG. 28 illustrates conceptually a trace representing a signal having a biphasic asymmetric rectangular waveform in which the first phase is cathodic and the second, anodic phase, is of the same width and larger amplitude in accordance with an embodiment of the present disclosure.
Figure 29:
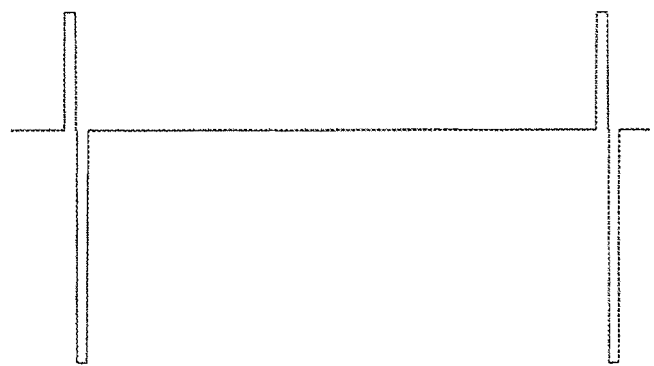
FIG. 29 illustrates conceptually a trace representing a signal having a biphasic asymmetric rectangular waveform in which the first phase is anodic and the second, cathodic phase, is of the same width and larger amplitude in accordance with an embodiment of the present disclosure.
Figure 30:
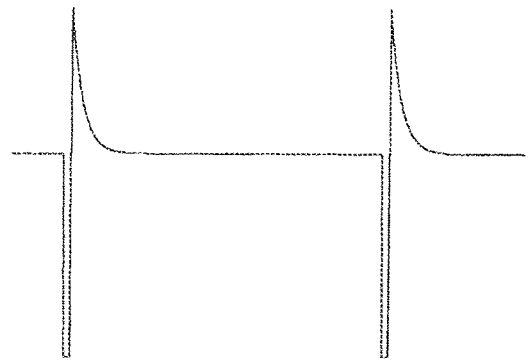
FIG. 30 illustrates conceptually a trace representing a signal having a biphasic asymmetric waveform in which the first phase is cathodic rectangular and the second, anodic phase, corresponds to a capacitive-coupled recovery to baseline in accordance with an embodiment of the present disclosure.
Figure 31:
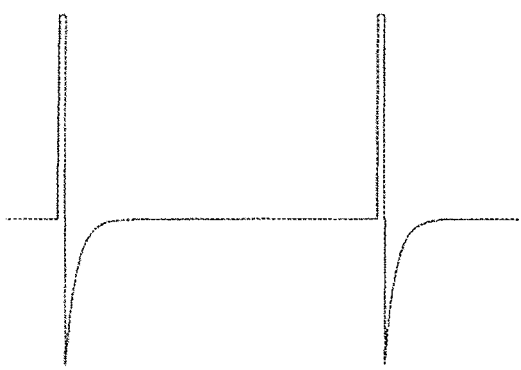
FIG. 31 illustrates conceptually a trace representing a biphasic asymmetric waveform in which the first phase is anodic and rectangular and the second, cathodic phase, corresponds to a capacitive-coupled recovery to baseline in accordance with an embodiment of the present disclosure.
Figure 32A:
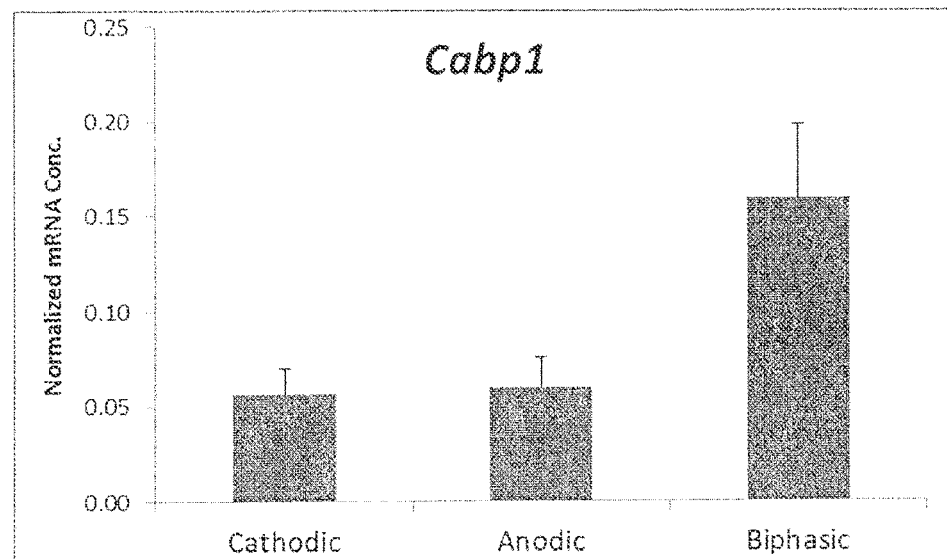
FIGS. 32(a)-(e) illustrate conceptually graphs of experimental results indicating how the polarity of the stimulating electromagnetic field signal influences gene expression.
Figure 32B:
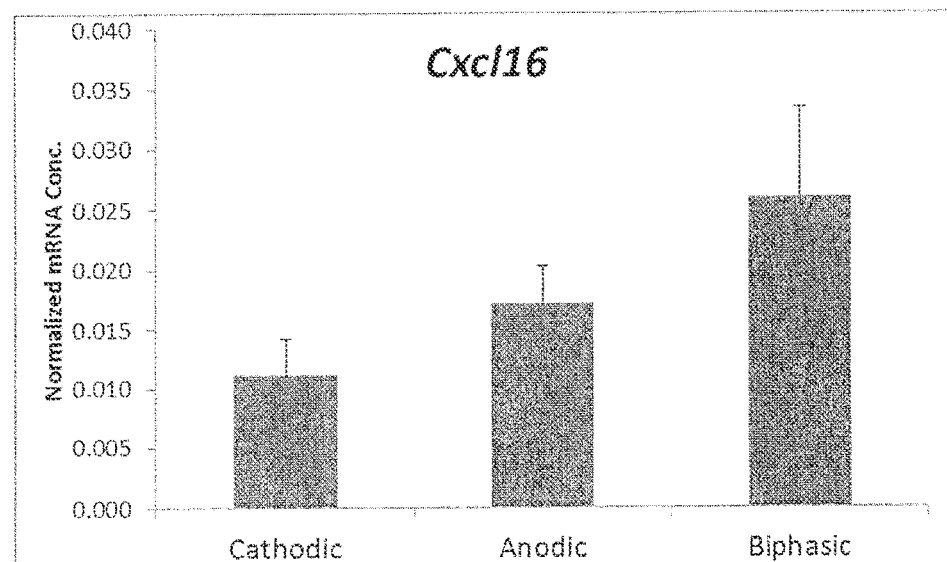
Figure 32C:
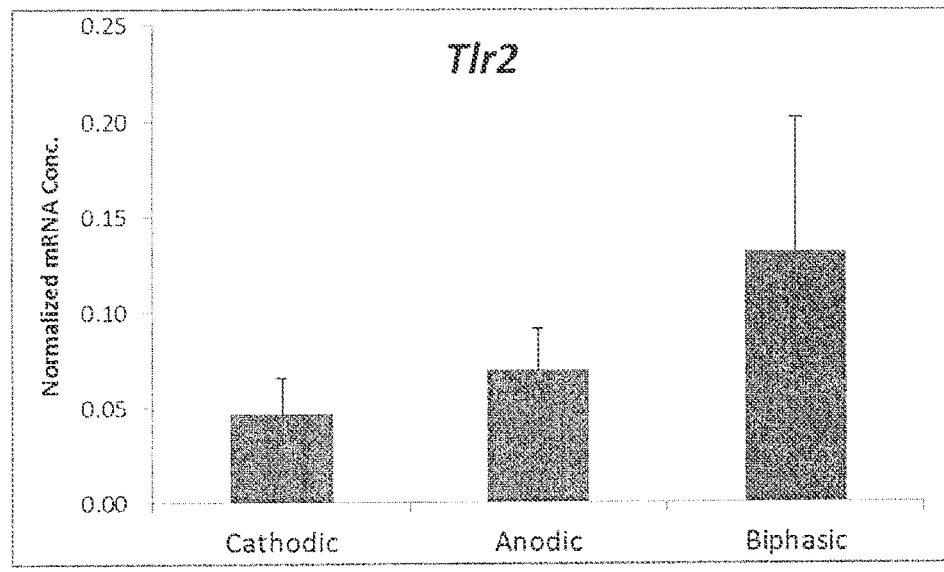
Figure 32D:
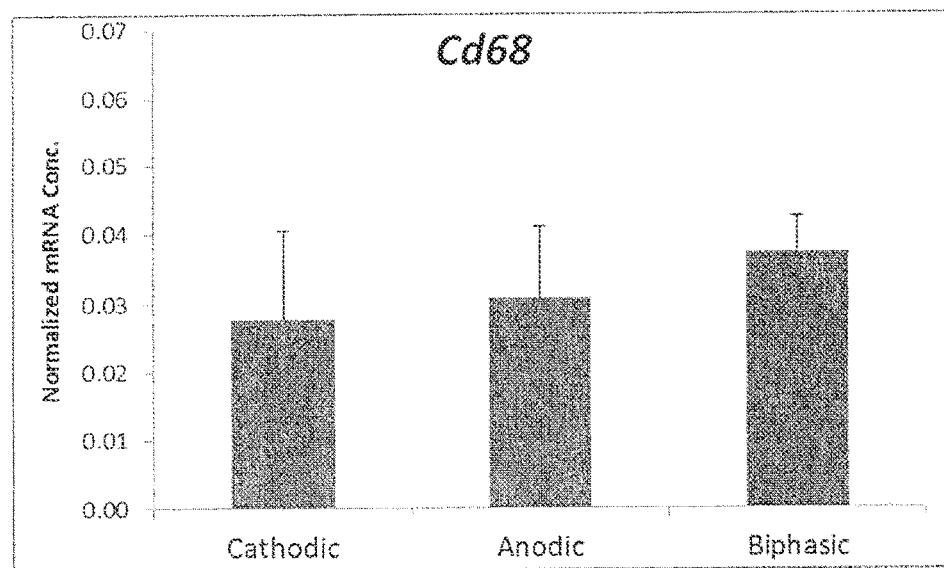
Figure 32E:
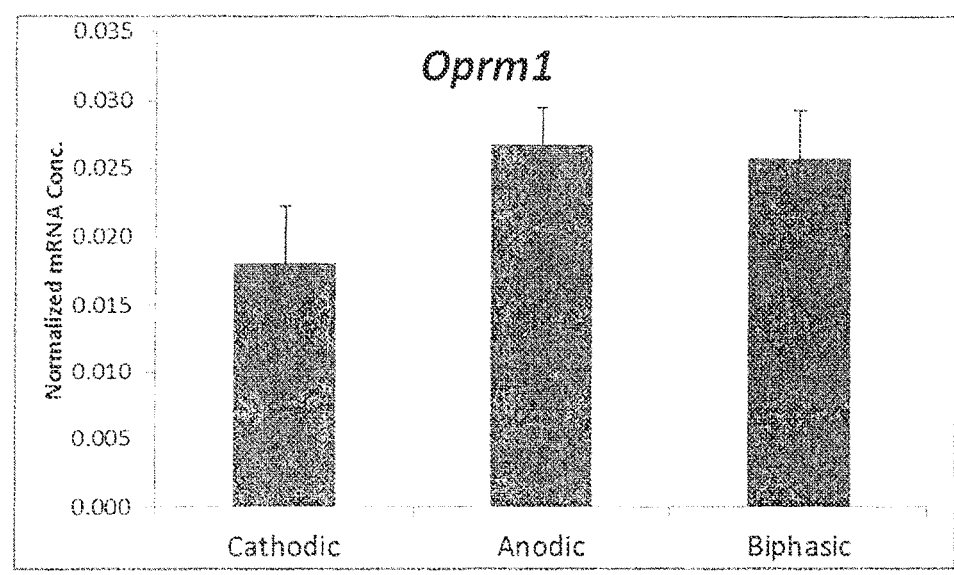

In yet another embodiment of multimodal modulation therapy, the priming signal may be monophasic, as illustrated in FIG. 18 or 19, or biphasic, as illustrated in FIGS. 20-31, in which the polarity of the first phase of the biphasic prime signal may be either cathodic or anodic. With this embodiment, the tonic signal may have waveform characteristics that are different from those of the priming signal. The tonic signal may be either monophasic, as illustrated in FIG. 18 or 19, or biphasic, as illustrated in FIGS. 20-31, with the polarity of the first phase of the biphasic tonic signal being either cathodic or anodic.

According to another aspect of the disclosure, a method for multimodal stimulation, referred to as "twin" stimulation utilizes two fields that are oscillating at the same frequency (F), which may be set to a value larger than used conventionally. The rationale is similar to the one used in the priming scheme, except that a frequency between 500 Hz and 1,500 Hz, for example, is used for both signals. In this case, the likelihood of stimulation via depolarization and gating is decreased. In a typical application some contacts in the electrode may be set to deliver charge-balanced, e.g. biphasic symmetric, biphasic asymmetric, capacitor coupled monophasic, pulses at a rate of between 1,200 Hz to 1,500 Hz, for example, and PW for each phase set in between 10 µs and a value defined by the frequency of the oscillation and the delay between phase changes. For example, for F=1,200 Hz and a delay of 10 µs, the maximum PW is 395 µs. The current or voltage amplitude required for perception threshold (PT) is determined and then the electrical signal delivered to the stimulator may be set above, below or at this value (% PT). The other contacts may be set to deliver a field of the same frequency, but PW and amplitude could be different, keeping in mind that the PW may be limited by frequency and the delay between phase changes. The second twin field could be fired synchronously, i.e. simultaneously, with the first twin field, or asynchronously, e.g. with a given time delay, relative to the first twin field.

The techniques disclosed herein may be achieved with minimally invasive procedures which are preferred over those that require extensive surgical intervention and healthcare expenses although in particular circumstances, a surgical implantation may be required. Electrical stimulation leads, similar to those illustrated in FIGS. 3A-B, can be used, but other designs having a different number of electrodes, size of the electrical contact, spacing between contacts, and geometrical arrangement of electrodes within an array may be utilized. In an embodiment, a lead comprises a cylindrical arrangement of multiple electrodes, e.g. between 4 and 16. The diameter of the lead may be small enough to allow for percutaneous implantation into the spinal canal using an epidural needle under standard clinical practice. The electrodes are made of biocompatible materials such as iridium-platinum alloys which are also resistant to corrosion. For example, a 50 cm long lead implemented with eight electrodes may have a diameter of 1.35 mm, with each cylindrical electrode having a length of 3.0 mm, and a spacing between electrodes of 4.0 mm. Conducting wires may run from the electrodes to the distal part of the lead into metal connectors. The wires may be enclosed within a triple-insulated containment made of a biocompatible durable polymer.

Figure 3A:
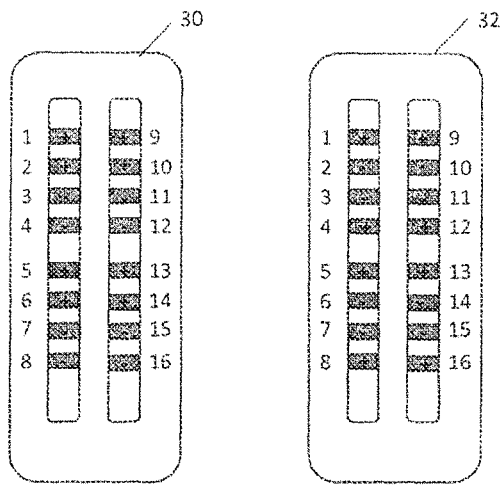
FIGS. 3A-B illustrate conceptually electrode arrays that may be utilized with a system in accordance with an embodiment of the present disclosure.
Figure 3B:
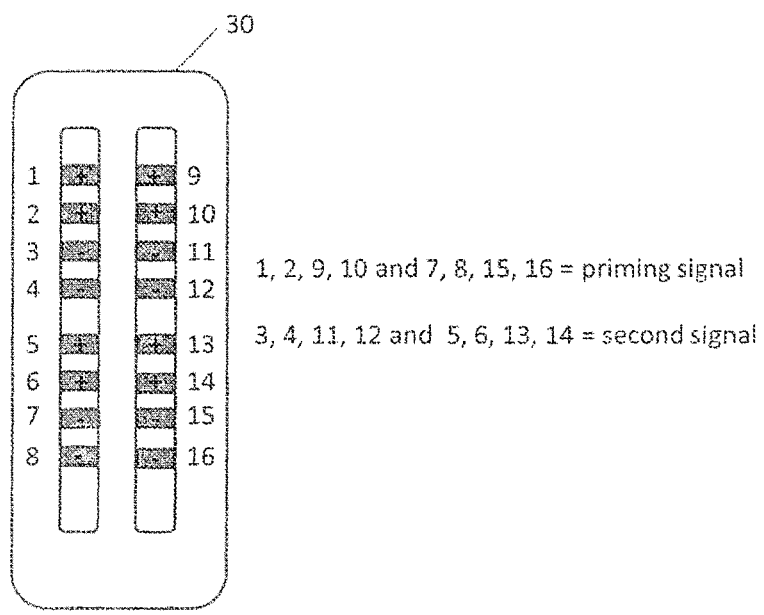

In the case of multimodal modulation of the spinal cord, various multi-contact leads can be positioned in the epidural space to stimulate the cell populations already described. In one particular arrangement, the leads can be positioned parallel to each other. FIG. 3A illustrates two eight-contact electrode arrays that can be used for the disclosed multimodal modulation techniques. Electrode contacts numbered 1-4 and 9-12 (using a traditional numbering of electrode contacts), located at the top (rostral) region may be used to deliver tonic pulses in the multimodal prime scheme, while eight electrode contacts at the bottom (caudal) numbered 5-8 and 13-16 may be used to deliver the priming pulses. Note that the polarity of the leads can also be customized during the programming stage, either as bipolar, monopolar, or guarded cathode configurations. Another example of a possible electrode array arrangement is shown in FIG. 38, in which the tonic electric field is surrounded by the electric field of the priming signal, allowing for priming of a larger section and tonic delivery in a smaller region. In another example, each individual electrode array could be set to deliver the electric fields parallel to each other.

Other arrangements may be used to stimulate different places along the spinal canal, e.g. the leads do not need to be parallel. For example, in one arrangement, one lead can be dedicated to deliver a signal (prime or twin) at the spinal cord at a given vertebral level, while the other provides a signal either more caudad or cephalad relative to the position of the other lead. Leads can be in principle located at any vertebral level in the spinal cord, or could also be positioned peripherally, because the principle behind multimodal modulation applies to peripheral glial cells that survey the axons.

Systems Components

FIG. 1 illustrates conceptually an embodiment of a non-implantable trialing system that may be utilized to perform the methods disclosed herein. The system comprises a pair of electrical leads 30 and 32, each of which may be implemented with an array of electrode contacts, a breakout box 18 and signal generators 17 and 19, as illustrated. Breakout box 18 is electrically coupled to leads 30 and 32 and signal generators 17 and 19 through appropriate connectors. The breakout box 18 and signal generators 17 and 19 may be placed in an enclosure referred to as an External Trial Stimulator (ETS) system 16. Each of generators 17 and 19 deliver a particular signal with parameters that can be set separately for each other.

Each of generators 17 and 19 may have the functional characteristics and architecture elements similar to generator 20 described herein without an exterior enclosure suitable for implantation into a patient. In one embodiment, system 16 may also include one or more of the modules described herein with reference to Implantable Multimodal Generator 20 and FIG. 2.

The ETS system 16 is electrically coupled to electrical leads, each of which may be implemented with an array of electrode contacts. In an embodiment, a pair of leads 30 and 32 is coupled to the ETS 16 using appropriate connectors as illustrated in FIG. 1. In another embodiment, a single lead implemented with an array of electrodes can be used. In a configuration for performing prime multimodal modulation, one of generators 17 or 19 may be configured to deliver a priming signal, for example 1,200 Hz, and the other generator may be configured to deliver a tonic signal, e.g. at 50 Hz. The breakout box 18 may be used to reconfigure the delivery of signals to the proper electrode contacts in leads 30 and 32. In the embodiment illustrated in FIG. 1, the electrode contacts 1-8 in electrode array 30 can be split such that electrode contacts 1-4 deliver a first signal, e.g. a tonic signal, different than a second signal delivered at electrode contacts 5-8 thereof, e.g. a priming signal. Similarly, electrode contacts 9-16 of electrode array 32 may be split such that electrode contacts 9-12 thereof deliver a signal similar to that delivered by electrode contacts 1-4 in electrode array 30, while electrode contacts 13-16 thereof deliver a signal similar to that delivered at electrode contacts 5-8 in electrode array 30, as illustrated. In other embodiments either the tonic signal or the priming signal may be sent to any other combination of electrode contacts.

Implantable Multimodal Generator

Figure 2:
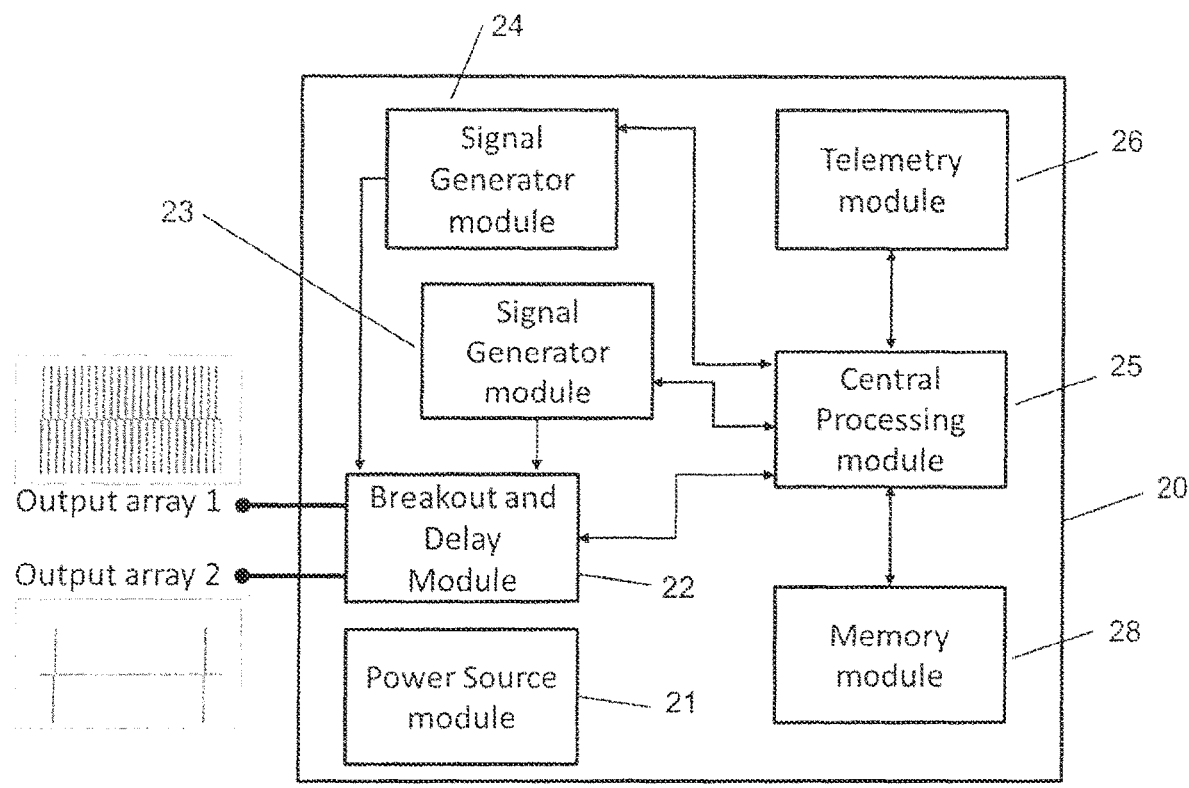
FIG. 2 illustrates a schematic circuit diagram of an implantable multimodal modulation device that may be utilized with a system in accordance with an embodiment of the present disclosure.

FIG. 2 illustrates conceptually a block diagram of the elements comprising an Implantable Multimodal Generator (IMG) 20. The generator circuitry may be hermetically sealed in a housing made of a durable biocompatible material, such as stainless steel or titanium. The generator 20 has an output interface for establishing electrical connection with arrays of electrodes implemented within the previously described leads 30 and 32 that deliver the multimodal signals to glial cells and neurons. In one embodiment, the implantable multimodal generator 20 comprises a central processing module 25, a memory module 28, a telemetry module 26, a power source module 21, signal generator module 23, signal generator module 24, and a Breakout and Delay module 22, including the output interfaces thereof.

The central processing module 25 may be implemented with a microprocessor integrated circuit or may comprise reduced functionality small-scale logic, but, in either implementation includes a wireless transceiver functionality that enables bidirectional wireless communication of information with an external programmer unit (not shown) or a user-controlled remote 36.

The memory module 28, which may be implemented with either RAM or ROM memory, may be used to store a modulation program, executable by central processing module 25, which generates functional information of the generator 20. The central processing module 25 is able to store and retrieve information from a memory module 28 as commanded by the user.

The telemetry module 26 is used to communicate via a wireless protocol with the external programmer unit (or control remote) and includes transceiver circuitry in order to conduct wireless communications with devices remote from generator 20 according to any number of established wireless protocols.

The power source module 21 may comprise a rechargeable battery and electronic circuity that distributes power from the battery to all the other components in the implantable multimodal generator 20.

The signal generator module 23 comprises electronic circuitry that allows the delivery of charge-balanced waveforms of any waveshape, including but not limited to biphasic or monophasic pulses, sinusoidal trains, sawtooth trains, triangle trains, and bursts thereof. In one embodiment, signal generator module 23 comprises electronic circuitry that allows the delivery of noise signals, such as white noise, with a constant power spectral density, or pink noise, with equal energy in octave intervals, or other noise signals in which the energy within the signal spectrum is distributed in other patterns. In one embodiment, a noise signal may be used as the priming mechanism in the techniques disclosed herein. The signal generator module 23 is able to deliver these waveforms at frequencies ranging from 1 Hz to 100 kHz. For pulse delivery, the signal generator module 23 is able to deliver rectangular pulse waves over a range of widths, e.g. as small as 1 µs and as large as 250 ms, depending on frequency. The signal generator module 23 is further capable of generating a range of interphase delays. The signal generator module 23 is designed to deliver a signal, with amplitude which is either voltage controlled or current controlled, over a range of values, e.g. 0 V to 30 V or 0 mA to 30 mA, respectively. The signal generator module 23 is also able to generate pulses with a duty cycle. The signal generator module 23 is controlled by the central processing module 25 according to parameters selected by the user in an external programmer unit (or control remote). Signal generator module 23 may be implemented with analog or digital circuitry or a combination thereof. Signal generator module 24 may be structurally and functionally similar or dissimilar to signal generator module 23, and may be independently controlled and programmed.

Figure 7:
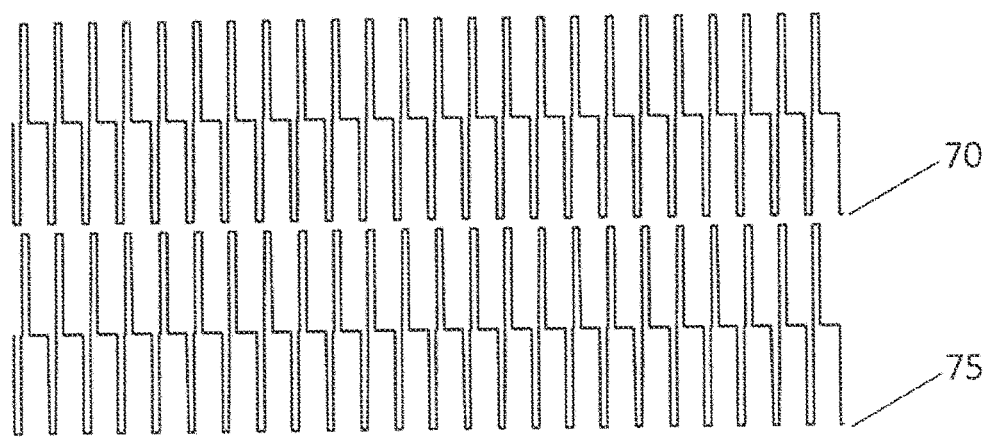
FIG. 7 illustrates conceptually a pair of traces representing signals that may be used in an example of twin multimodal modulation in accordance with an embodiment of the present disclosure.

The breakout and delay module 22 comprises an accurate timer electronic circuitry that can slave one of signal generator modules 23 or 24 to the other, so that a delay can be produced between signals generated therefrom such that a synchronized delivery of such signals can be programmed by a user, for example as shown in FIG. 7. The breakout and delay module 22 also incorporates an electronic circuitry, called breakout, that allows for the user to select an option in which the output array 1 delivers the a particular signal to all top (rostral during spinal cord stimulation) electrode contacts of a pair of electrode arrays (for example, tonic 50 Hz, 250 µs pulse width, 3.0 mA), while output array 2 delivers a different signal to all bottom electrode contacts of a pair of electrode arrays (for example, a priming signal of 1,200 Hz, 100 µs pulse width, 3.5 mA). An example of this option is shown in FIG. 3A. Another option is one illustrated in FIG. 3B. The breakout option can be bypassed. In that case, all contacts in a given electrode array will be set at the same modulation parameters as delivered by, for example, signal generator module 23. All contacts in the other electrode array will be set to same modulation parameters as delivered by the other Signal Generator module.

In one embodiment, all or most of the functional blocks of generator 20 may be fabricated on a single integrated circuit chip including a microprocessor and associated memory, wireless transducer and one or more digital oscillators. Alternatively, the digital oscillators may be replaced with wave tables having stored therein mathematical descriptions of various waveform data values which are convertible into analog signals using a digital to analog converter integrated into or associated with the processor module 25 or signal generator modules 23 or 24, depending on their respective implementations. Such wavetables may be stored in processor module 25 or memory module 28. In embodiments the various modules of IMG 20 may communicate over a central bus internal thereto or may have dedicated direct connections therebetween, or any combination thereof.

In one embodiment, IMG 20 or ETS 16 may be programmed by a clinician using software that allows control of all the aspects of the system. The software may be accessible in a computer-based interface called the Clinician Programmer (CP) software. The software may be implemented with wireless communication protocols for remote access of the IMG 20 or ETS 16. ETS 16 may also be provided with a network port such as a USB or micro-UBS port for interacting with the CP. In the case of IMG 20, the CP software enables the clinician to communicate with central processing module 25 to define a set of parameters, e.g. any of amplitude, frequency, phase, phase polarity, waveform shape, and width (rectangular waveform), etc., of the signal generated by signal generator modules 23 or 24 and to further define the parameters of their relative timing by defining the operational parameters of breakout and delay module 22. Such defined parameter sets may be stored as one or more configuration programs in memory module 28 or in memory associated with central processing module 25. In one embodiment, one or more configuration programs may be stored in memory associated with remote controller 36 and the parameters thereof transmittable to IMG 20 via telemetry module 26 for control of generator modules 23 or 24 and of breakout and delay module 22. The CP software may enable the clinician to further define which parameter the patient may control with the remote controller 36 and to define any limits on such parameter. For example, the clinician can set and store a configuration program #1 with parameters that provides prime multimodal stimulation consisting of priming with a biphasic symmetric rectangular pulsed signal set at 1,500 Hz, 200 µs PW, and current-based amplitude set as a %PPT, and a tonic signal delivering biphasic symmetric rectangular pulses at 50 Hz, 400 µs PW, and current-based amplitude set as a %PT. These signals can be delivered to a particular set of electrodes in the leads. The clinician can also set and store a configuration program #2 that provides twin multimodal stimulation consisting of asynchronous biphasic symmetric rectangular pulses at 1,500 Hz, one of them at 200 µs PW and the other at 100 µs PW and each set at its own current-based amplitude set a particular %PT. These signals can be delivered to a particular set of electrodes in the leads which may be different to that used in configuration program #1. The system allows for setting and storing additional configuration programs deemed necessary for the clinician and according to the storage capacity of the memory module 28. Limited control of the multimodal configuration programs may be available to the patient via a remote controller 36. In one embodiment, the clinician can access one or more configuration programs using the CP to control any of the parameters of a configuration program already stored in the ETS 16 or IMG 20. The patient may be able to browse and/or select any available configuration program with the remote controller 36. The patient may be able to change the current-based amplitude of any particular configuration program up to a particular setting determined by the PPT or PT in order to optimize pain relief, for example. Note the remote controller 36 may be provided with a simple interface, such as a selector switch, or dial to select the appropriate configuration program, or a more sophisticated user interface including a visual display with directional keys or touch sensitive menus.

Figure 4:
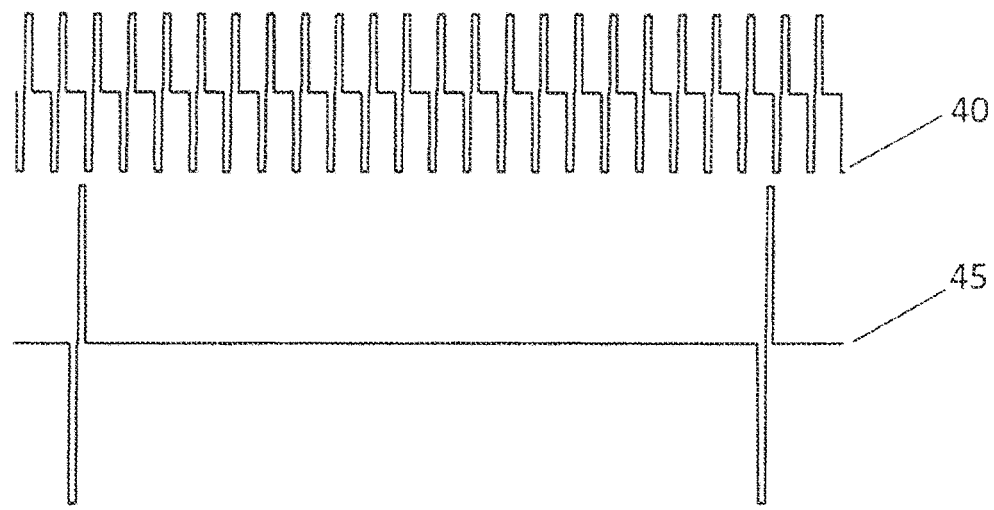
FIG. 4 illustrates conceptually a pair of traces representing signals that may be used in an example of prime multimodal modulation in accordance with an embodiment of the present disclosure.

FIG. 4 illustrates conceptually a pair of traces representing signals 40 and 45 used in an example of prime multimodal modulation. Signal 40 functions as a priming waveform and may comprise, for example, biphasic rectangular pulses with a frequency of 1,200 Hz, PW=200 µs and interphase delay of 20 µs. Signal 45 functions as the tonic waveform and may comprise, for example, biphasic rectangular pulses with a frequency of 50 Hz, PW=200 µs and interphase delay of 20 µs. In this example, the amplitude of the tonic waveform is set to be larger than the amplitude of the priming waveform. Signals 40 and 45 have been offset in FIG. 4 for visual clarity. Note in FIGS. 4-8 the signals representing the tonic and priming waveforms are offset for visual clarity, such offset not meant to limiting in any matter.

Figure 5:
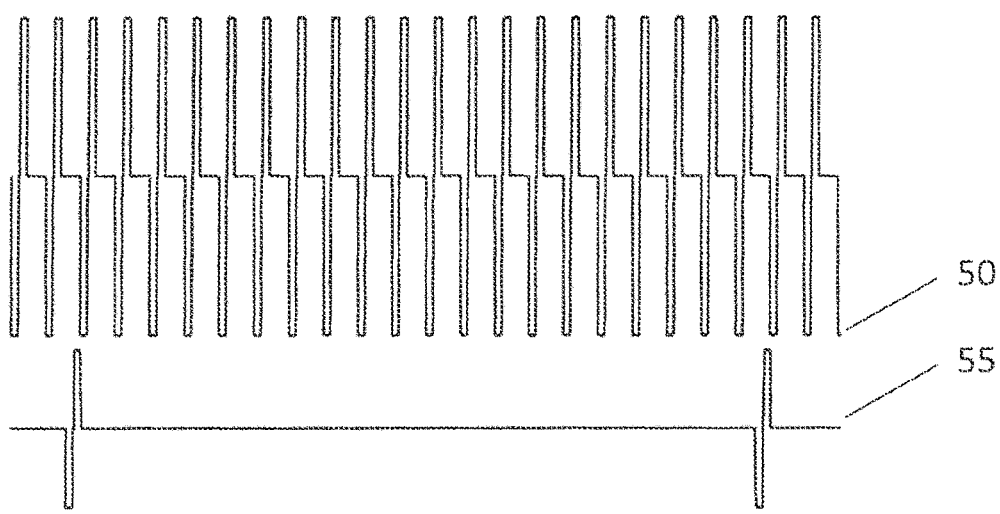
FIG. 5 illustrates conceptually a pair of traces representing signals that may be used in an example of prime multimodal modulation in accordance with an embodiment of the present disclosure.

FIG. 5 illustrates conceptually a pair of traces representing signals 50 and 55 used in an example of prime multimodal modulation. Signal 50 functions as a priming waveform and may comprise, for example, biphasic rectangular pulses with a frequency of 1,200 Hz, PW=200 μs and interphase delay of 20 μs. Bottom trace is the tonic waveform and may comprise, for example, biphasic rectangular pulses with a frequency of 50 Hz, PW=200 μs and interphase delay of 20 μs. In this example the amplitude of the tonic waveform is set to be smaller than the amplitude of the priming waveform. Signals 50 and 55 have been offset in FIG. 5 for visual clarity.

Figure 6:
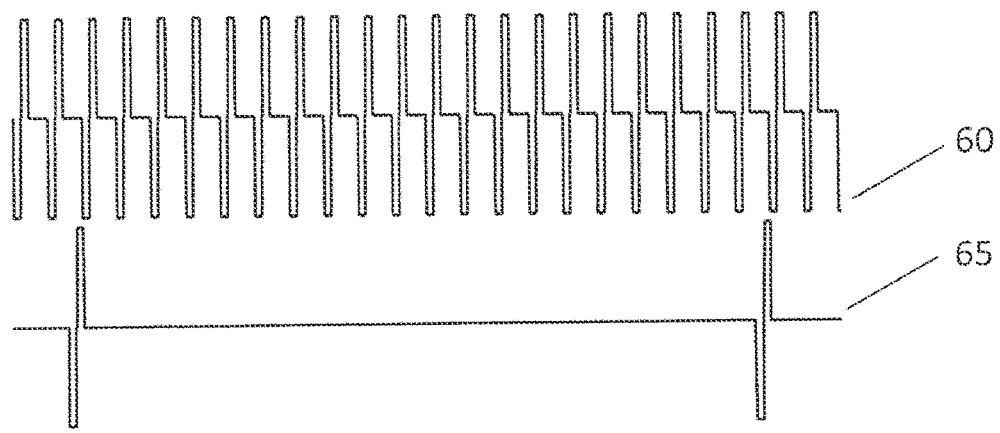
FIG. 6 illustrates conceptually a pair of traces representing signals that may be used in an example of prime multimodal modulation in accordance with an embodiment of the present disclosure.

FIG. 6 illustrates conceptually a pair of traces representing signals 60 and 65 used in an example of prime multimodal modulation. Signal 60 functions as a priming waveform and may comprise, for example, biphasic rectangular pulses with a frequency of 1,200 Hz, PW=200 μs and interphase delay of 20 μs. Bottom trace is the tonic waveform and may comprise, for example, biphasic rectangular pulses with a frequency of 50 Hz, PW=200 μs and interphase delay of 20 μs. In this example the amplitude of the tonic waveform is set to be equal to the amplitude of the priming waveform. Signals 60 and 65 have been offset in FIG. 6 for visual clarity.

FIG. 7 illustrates conceptually a pair of traces representing signals 70 and 75 used in an example of twin multimodal modulation. Both signals 70 and 75 comprise, for example, biphasic rectangular pulses with a frequency of 1,200 Hz, PW=200 μs and interphase delay of 20 μs. In this example, signals 70 and 75 are synchronous to each other and the amplitude of the waveforms is set to be equal. Signal 70 and 75 have been offset in FIG. 7 for visual clarity.

Figure 8:
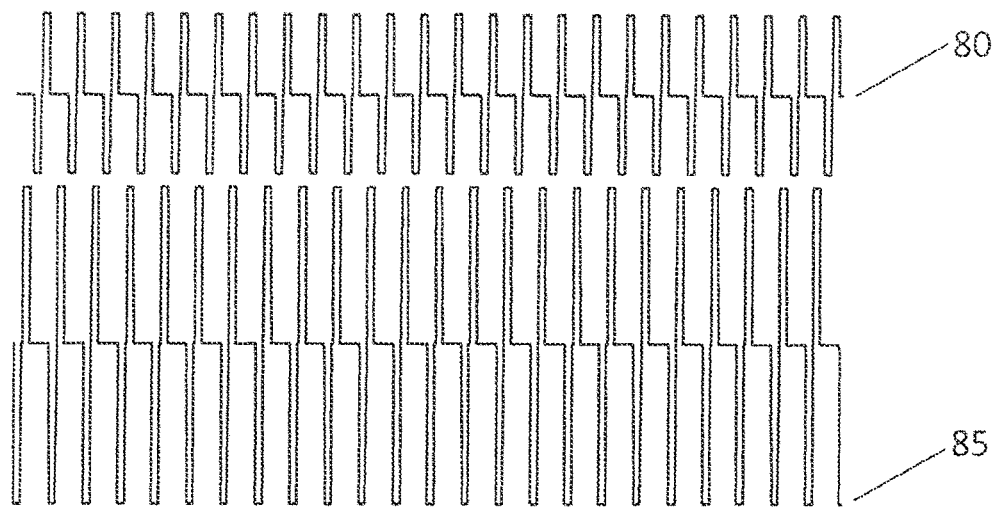
FIG. 8 illustrates conceptually a pair of traces representing signals that may be used in an example of twin multimodal modulation in accordance with an embodiment of the present disclosure.

FIG. 8 illustrates conceptually a pair of traces representing signals 80 and 85 used in an example of twin multimodal modulation. Both signals 80 and 85 may comprise, for example, biphasic square pulses with a frequency of 1,200 Hz, PW=200 μs and interphase delay of 20 μs. In this example signals 80 and 85 are asynchronous with each other and the amplitude of one of the signals is set to be larger than the other. Signals 80 and 85 in FIG. 8 have been offset for visual clarity.

Figure 9:
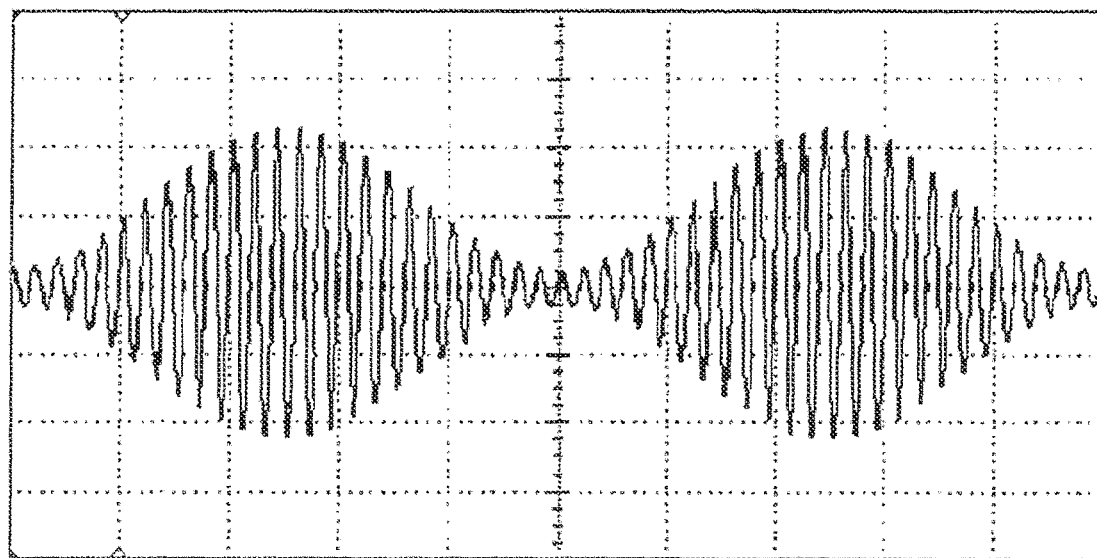
FIG. 9 illustrates conceptually an amplitude modulated signal that may be utilized for multimodal modulation in accordance with an embodiment of the present disclosure.
Figure 10:
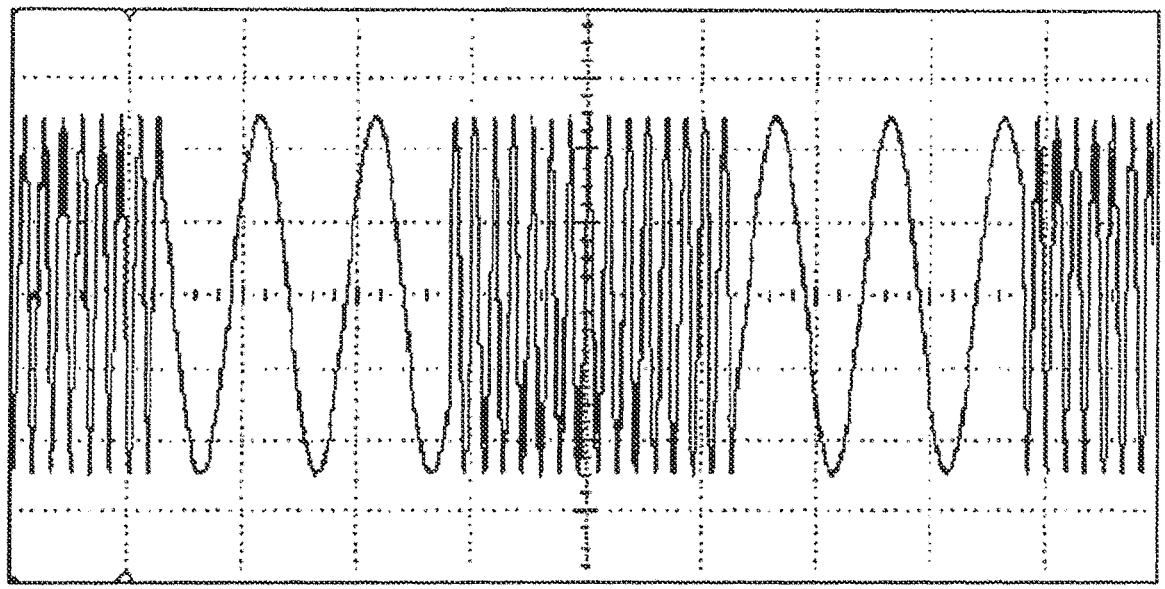
FIG. 10 illustrates conceptually a frequency modulated signal, with a carrier frequency larger that the modulating frequency, that may be utilized for multimodal modulation in accordance with an embodiment of the present disclosure.
Figure 11:
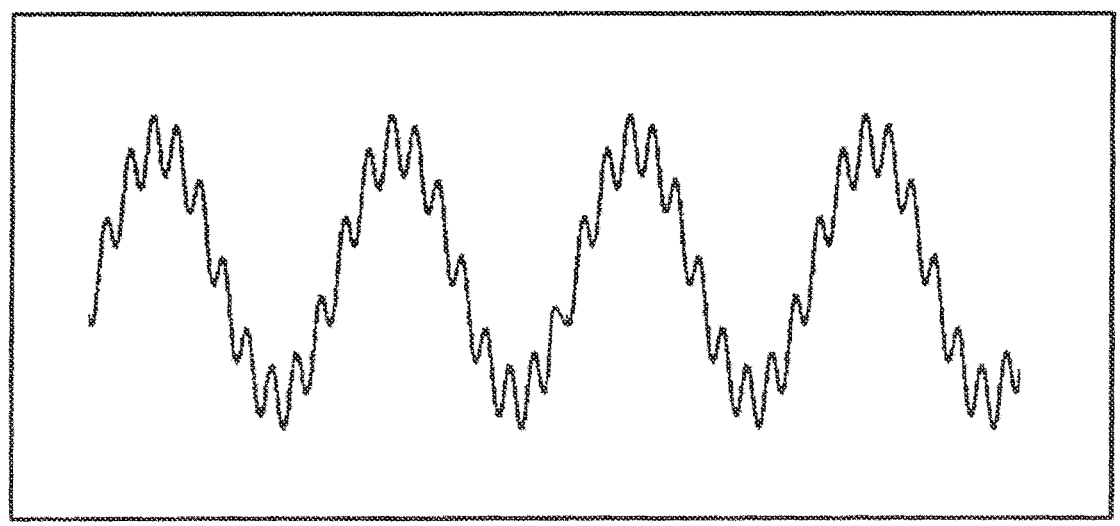
FIG. 11 illustrates conceptually a frequency modulated signal, with a carrier frequency smaller than the modulating frequency, that may be utilized for multimodal modulation in accordance with an embodiment of the present disclosure.
Figure 12:
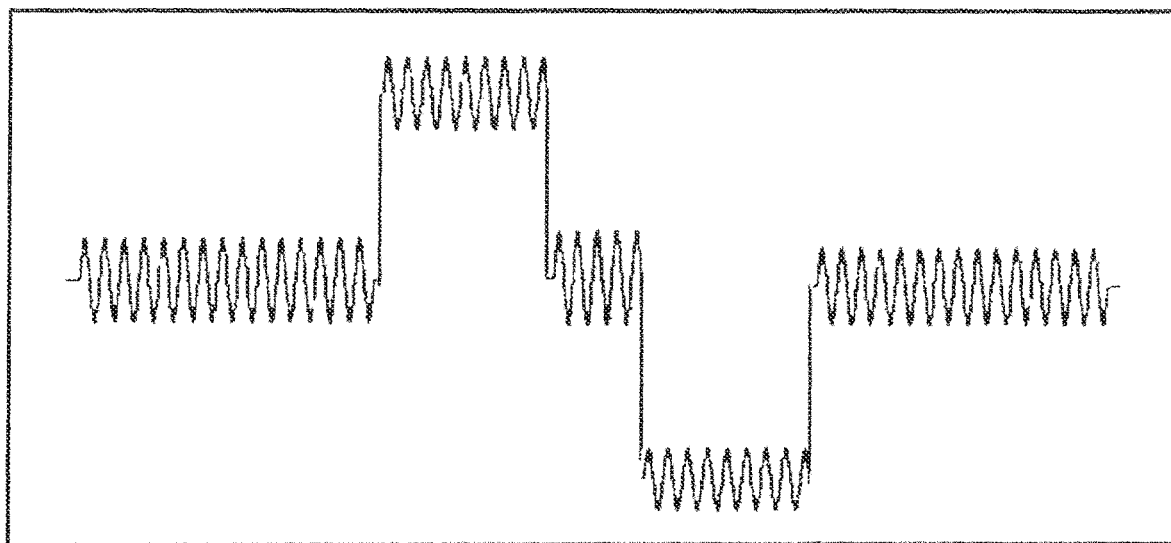
FIG. 12 illustrates conceptually a dual combined signal, biphasic pulse example, that may be utilized for multimodal modulation in accordance with an embodiment of the present disclosure.
Figure 13:
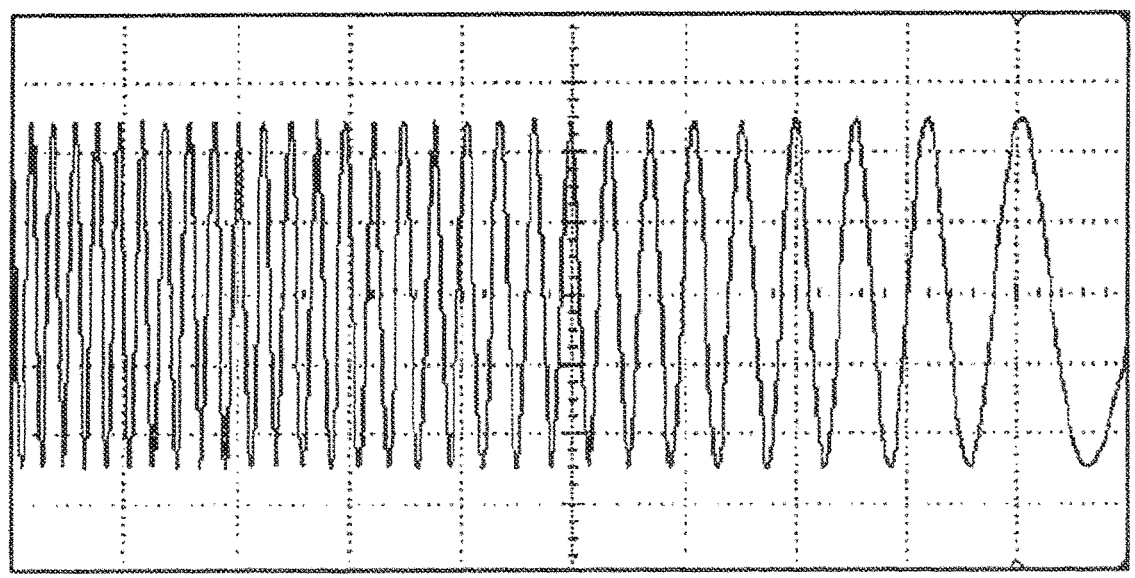
FIG. 13 illustrates conceptually a signal with a continually changing frequency that may be utilized for multimodal modulation in accordance with an embodiment of the present disclosure.

According to another aspect of the disclosure, the benefits and effects of multimodal modulation, both the prime multimodal technique and the twin multimodal technique, as described herein, may be achieved with a single composite modulation/stimulation signal which has rhythmically varying characteristics, and, therefore, alternating magnetic field characteristics which achieve the same results as two separate signals. In such an embodiment, a composite signal characterized by typically alternating characteristics is utilized to obtain the same stimulation and modulation of the interaction between glial cells and neurons. Techniques for combining the separate signals into a single composite signal may include amplitude modulation, frequency modulation, signal summing, and generation of customized signals with any of periodic or aperiodic characteristics. In addition, pulse width modulated signals having variably changing harmonic energy content may similarly be utilized to achieve the desired multimodal stimulation of glial and neuronal cells. FIGS. 9-13 illustrate conceptually examples of amplitude modulated, frequency modulated, dual combined sinusoidal, dual combined biphasic rectangular pulse, and frequency changing signals, respectively, that may be utilized for multimodal modulation In accordance with an embodiment of the present disclosure the central processor module 25 of multimodal generator 20 may access stored numeric data mathematically describing wave shapes for one or more signals and may generate from such data step functions emulating signals at different frequencies. The processor performs algorithmic manipulation of such data to achieve the desired signal processing results. Digital to analog converters associated with the central processing module 25 may convert the processed signal into a single output having the correct amplitude for coupling to one or both electrodes 30 and 32. In this manner, the interactive effects of two separate signals may be achieved with a single electrical signal capable of stimulating/modulating the interaction between glial cells and neurons in a manner which emulates the use of two separate signals. In composite signals emulating a frequency modulated prime multimodal modulation signal, either constituent signal component, e.g. the priming signal or the tonic signal, may function as the program or carrier signals in a frequency modulation algorithm. For example, a frequency modulated multimodal signal can have a carrier frequency larger (e.g. 1,000 Hz) than the modulating frequency (e.g. 50 Hz) resulting in a stimulating signal as illustrated in FIG. 10. In another example, a frequency modulated multimodal signal can have a carrier frequency smaller (e.g. 50 Hz) than the modulating frequency (e.g. 1,000 Hz) resulting in a stimulating signal as illustrated in FIG. 11. In an example of an amplitude modulated multimodal signal, the carrier frequency can have a carrier priming frequency of, for example, 1,000 Hz, and a modulating frequency of, for example, 50 Hz, resulting in a stimulating signal as illustrated in FIG. 9.

Figure 14:
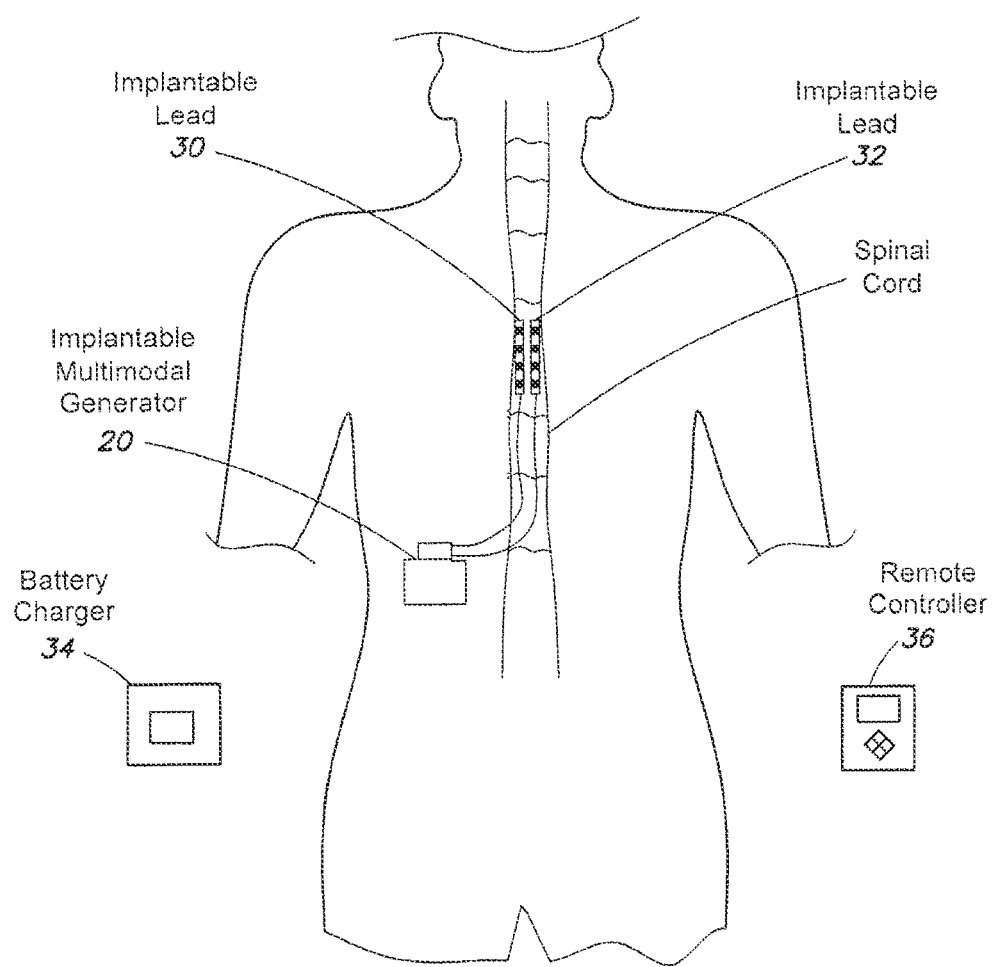
FIG. 14 illustrates conceptually the placement of an implantable system with a human subject in accordance with an embodiment of the present disclosure.

FIG. 14 illustrates conceptually another embodiment of an implantable system with a human subject in prone position. Shown is an example of an implantable system in which both leads 30 and 32 are positioned above the dorsal spinal cord at a particular vertebral level. A programmable implantable multimodal generator (IMG) 20 is attached to the leads using conductive cables and is powered by a rechargeable or non-rechargeable long-life battery contained within the Power Source module 21, within the implantable multimodal generator 20. An external battery charger 34 may be used for recharging of the generator using inductive, i.e. wireless, charging. A wireless remote control 36, which may be implemented with any number of wireless communication protocols, including Bluetooth or others, may be used to communicate with IMG 20 to enable a patient's adjustment of parameters at the discretion of the physician. The system may be programmed using an external programmer unit, such a computer (not shown) that can transmit information to the IMG 20 via wireless communication protocols.

Figure 15:
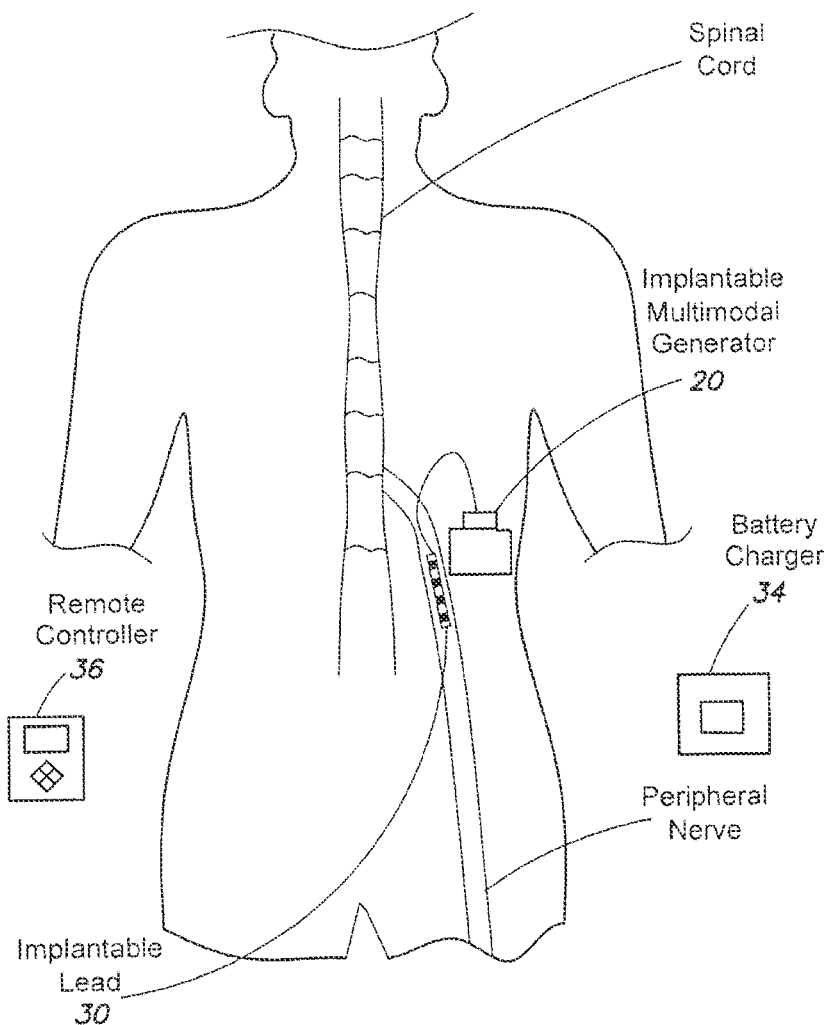
FIG. 15 illustrates conceptually the placement of an implantable system with a human subject in accordance with an embodiment of the present disclosure.

FIG. 15 illustrates conceptually another embodiment of an implantable system with a human subject in prone position. Shown is an example of an implantable system, similar to that illustrated with reference to FIG. 14 herein, in which leads are positioned in the neighborhood of a peripheral nerve.

EXAMPLE 1

Figure 16:
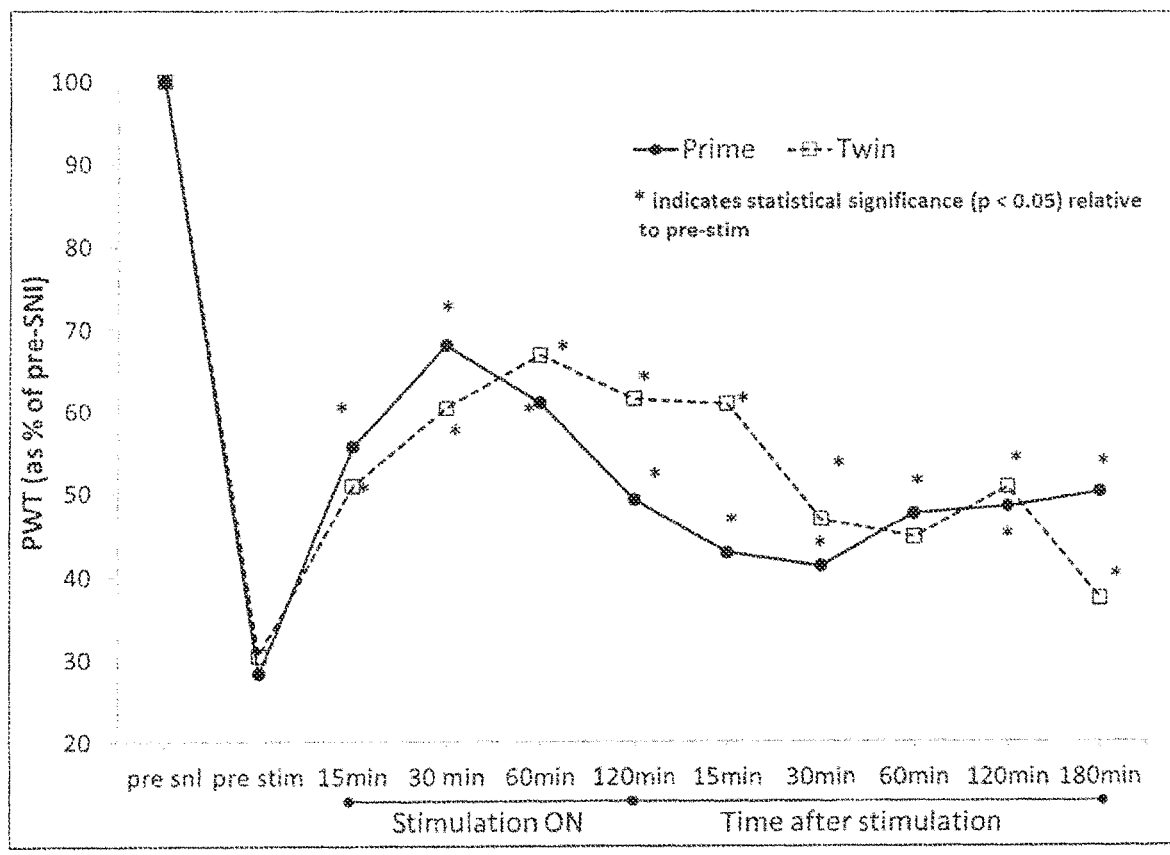
FIG. 16 illustrates conceptually a graph of results achieved in a pre-clinical animal study utilizing systems and methods in accordance with the present disclosure.

Referring to FIG. 16, an initial pilot study using an animal model for neuropathic chronic pain was carried out (n=29). In this study, a peripheral nerve injury was surgically induced by transecting the tibial and peroneal branches of the sciatic nerve at the point of trifurcation while sparing the sural nerve (spared nerve injury, SNI, model). After four days of transection, the subject develops mechanical and thermal hypersensitivity (allodynia), which is considered pain-like behavior. Subjects were implanted with a small cylindrical four-contact lead fitted surgically into their epidural space at the vertebral level corresponding to the innervation of the sciatic nerve. At day four post-surgery subjects were behaviorally tested using von Frey filaments. These filaments of different tensile strength are used to measure the sensitivity of a skin area affected by the nerve injury to mechanical stimulation. In the SNI model, the plantar area of the hind paw ipsilateral to injury becomes hypersensitive. A hypersensitive subject will withdraw its paw upon stimulation with a filament of very low tensile strength. Mechanical hypersensitivity was evident in the ipsilateral hind paw in comparison to the contralateral one, which was used as a normal behavior control. In a particular example of prime multimodal stimulation, electrode contacts 3 and 4 were connected to a current source delivering a charge-balanced biphasic symmetric rectangular pulse oscillating at 1,200 Hz and a PW of 30 μs at an amplitude of 0.1 mA (33% motor threshold, MT). This priming signal was set on for 10 minutes before a tonic signal was sent simultaneously at electrode contacts 1 and 2. This tonic signal was a charged balanced biphasic symmetric rectangular pulse oscillating at 50 Hz, PW of 50 μs and amplitude of 0.2 mA (66% MT). In a particular example of twin multimodal stimulation, electrode contacts 3 and 4 were connected to a current source delivering a charge-balanced biphasic rectangular pulse oscillating at 1,200 Hz and a PW of 30 μs at an amplitude of 0.1 mA (33% motor threshold, MT). This signal was set on for 10 minutes before another charged balanced biphasic rectangular pulse oscillating at same frequency and PW but different amplitude of 0.2 mA (66% MT) was sent simultaneously at electrode contacts 1 and 2. In either case, electrical stimulation was on continuously for two hours and behavioral testing for mechanical sensitivity was performed every fifteen minutes while the subject was being stimulated. Behavioral testing was continued every fifteen minutes after stimulation was turned off for one hour and then every hour until three hours post stimulation. FIG. 16 shows the results as an average of the various recordings obtained from nine subjects.

Behavioral data indicates that multimodal stimulation improves mechanical allodynia after fifteen minutes of stimulation with the improvement lasting for more than one hour after the stimulation is turned off, indicating that there is a residual effect of the applied fields which suggest modulation of the nervous system.

EXAMPLE 2

In the example, the effect of spinal cord stimulation on gene expression in the ipsilateral dorsal spinal cord (DC) upon induction of chronic neuropathic pain after peripheral nerve injury was investigated. Specifically, in the example we compared the full genome of one the most commonly used rodent model for chronic neuropathic pain (spare nerve injury, SNI) upon continuous SCS relative to sham animals, i.e. animals in which pain model was induced, were implanted, but not stimulated.

The full genome microarray kit available for the laboratory rat used comprised about 21,000 genes. Enrichment analysis based on clustering statistics (using WGCNA) allowed for the identification of modules (or subsets) that contain genes that are highly correlated to each other in terms of biological role. Gene ontology analysis allowed for the grouping of genes within a module in terms of more specific biological processes and molecular functionality. Further refinement allows for the identification of key genes within a particular pathway.

It was found by comparison of the genome of the treated animals that SCS upregulates and down-regulates genes implied in various interrelated processes, as described herein.

Comparative Genomics at the Spinal Cord

Considering that stimulation occurs atop the dorsal region of the spinal cord, we concentrated effort on elucidating the role of genes on molecular functionality and biological functions associated to this tissue. WGCNA identified that SCS significantly upregulated genes involved in activation of the immune system (false discovery rate (FDR) adjusted P-value=0.016); while down-regulating genes that are involved in phosphorylation and activities related to transmembrane transport (FDR P-value=0.011) as well as regulation of neuronal activity including regeneration and development. Refinement of the data identified 52 key genes. Out of these, the following are noteworthy, since they are involved in the process of glial activation, immune response and neuronal activity:

Calcium binding protein (cabp1): This gene is down-regulated by SCS. The protein associated to this gene regulates calcium-dependent activity of inositol 1,4,5-triphosphate (ITP) receptors. This receptor is involved in the signaling between astrocytes via calcium waves, which play a key role in the intercellular communication that propagates astrocyte activation. Down regulation of this gene should diminish the activation of astrocytes that is conducive to synaptic reshaping that develops into a chronic pain state.

Toll-like receptor 2 (tlr2): This gene is up regulated by SCS. Toll-like receptor2 is expressed by activated glial cells. This gene is expressed in microglia and astrocytes, but expression in activated microglia is larger than expression in astrocytes. The protein associated to the gene induces a cascade of events that may lead to the secretion of anti-inflammatory cytokines, such as IL-10.

Chemokine cxcl16: This gene is up regulated by SCS. This is a transmembrane chemokine which drives the interplay between glial cells and neurons as a result of stimulus. Cxcl16 is expressed by microglia and astrocytes as a neuroprotective agent. Up-regulation of this gene by SCS is indicative of a neuroprotective process in the spinal cord likely involving the modulation of microglia.

Glial maturation factor (Gmfg): This gene is up regulated by SCS. This gene has been thought to be involved in glial differentiation and neural regeneration. There is not much known about this gene. Its up regulation by SCS may be associated to glial activation processes that may lead to neuronal regeneration.

Other key genes up-regulated or down-regulated by spinal cord stimulation are described with reference to Table 1-1 below:

TABLE 1-1

| Process | Gene | Description | Notes |
|---|---|---|---|
| \multicolumn{4}{c}{Selected Genes up-regulated by SCS} | | | |
| Inflammation and immune response | Ly86 | lymphocyte antigen 86 | Cooperate with toll like receptor to mediate the innate immune response |
| | Cd68 | Cd68 molecule | Phagocytic activities of tissue macrophages |
| | Apbb1ip | amyloid beta (A4) precursor protein | Signal transduction from Ras activation to actin cytoskeletal remodeling |
| | Casp1 | caspase 1 | Cleaves IL-1 beta |
| | lfi30 | interferon gamma inducible | MHC class II-restricted antigen processing |
| | Cd53 | Cd53 molecule | Mediate regulation of cell development, activation, growth and motility |
| | Tnfaip812 | tumor necrosis factor, alpha-induced protein | Regulator of innate and adaptive immunity by maintaining immune homeostasis |
| | 111b | interleukin 1 beta | Mediator of the inflammatory response. Induces cyclooxygenase-2 (COX2) to contribute to inflammatory pain. |
| | Cxcl17 | chemokine (C-X-C motif) ligand 17 | May be a chemokine regulating recruitment of monocytes and immature dendritic cells |
| | ltgb2 | integrin, beta 2 | Participate in cell adhesion as well as cell-surface mediated signaling |
| | Timp1 | TIMP metallopeptidase inhibitor 1 | Inhibitors of the matrix metalloproteinases, involved in degradation of the extracellular matrix |
| | Tnfsf12 | Tumor Necrosis Factor (Ligand) Superfamily, | Cytokine that belongs to tumor necrosis factor ligand family. It can apoptosis via multiple pathways of cell death in a cell type-specific manner. |
| | 112rg | Interleukin 2 Receptor, Gamma | Common subunit for the receptors for a variety of interleukins |
| \multicolumn{4}{c}{Selected genes down-regulated by SCS} | | | |
| Ion channel regulation | Wwp1 | WW domain containing E3 ubiquitin protein ligase 1 | Ubiquitinates and promotes degradation of SMAD2 in response to TGF-beta signaling |
| | Micu3 | Mitochondrial calcium uptake family | Essential regulator of mitochondrial calcium uptake under basal conditions |
| | Grin2a | Glutamate receptor, ionotropic, N-methyl D- aspartate 2A | Receptor activation requires binding of glutamate and glycine, leads to an influx of calcium into postsynaptic region activating pathways. NMDA receptors have a critical role in excitatory synaptic transmission and plasticity in the CNS. |

TABLE 1-1-continued

| Process | Gene | Description | Notes |
|---|---|---|---|
| Binding and metabolic pathways | Amph | Amphiphysin | Associated with the cytoplasmic surface of synaptic vesicles |
| | Gabrg1 | Gamma-Aminobutyric Acid (GABA) A receptor, 1 | Protein encoded by this is an integral membrane protein and inhibits neurotransmission by |
| | Gabra2 | Gamma-Aminobutyric Acid (GABA) A Receptor, Alpha 2 | to the benzodiazepine receptor and opening an integral chloride channel |
| | Gria3 | Glutamate receptor, ionotropic, AMPA 3 | Receptor for glutamate, functions as ligand-gated ion channel in the CNS, plays an important role in excitatory synaptic transmission |
| Cell growth | Kcna1 | Potassium Voltage-Gated Channel, Shaker-Related Subfamily | Mediates the voltage-dependent potassium ion permeability of excitable membranes |
| | Kifc3 | Kinesin Family Member C3 | Molecular motor that use ATP hydrolysis to translocate cargoes along microtubules |
| ATP related, transmembrane/ transporter activity | lgsf1 | Immunoglobulin Superfamily | Thought to participate in the regulation of interactions between cells |
| Cell regulation | Oprm1 | Opioid Receptor, Mu 1 | Principal target of endogenous opioid peptides and opioid analgesic agents such as beta-endorphin and enkephalins. |

Many of the genes involved in the inflammatory and immune response are associated to glial activity. Peripheral nerve injury is accompanied by regulation of genes and proteins not only in the site of injury, but also in the afferent ipsilateral CNS structures such as the DRG and the spinal cord. We recently obtained the proteomics in the spinal cord and DRG of the SNI animal model for neuropathic pain. This study indicates that there are transport and translocation of proteins along the axon towards the soma, and then reciprocal protein transport back to the periphery to induce axon regeneration. Interestingly, the spinal cord presents with neuroprotective proteins, some associated to glial cell activation. The activation of glial cells following injury induces a cascade of events including an inflammatory and immune response, which then develops into peripheral sensitization that is conducive to ectopic firing of neurons. The alarm eventually extends to the CNS at the level of the spinal cord, where the microglia would try to protect the integrity of the system. Eventually, glial cells overreact and induce the release of factors that reshape the synapses. These changes in the synaptic plasticity manifest as chronic pain.

The results indicate that electrical stimulation of the spinal cord elicits the regulation of genes and proteins that modulate the interactions between glial cells and neurons. It is plausible that these molecular events produce analgesia.

EXAMPLE 3

The effect of phase polarity on the modulation of genes previously presented was carried out using an animal model of chronic neuropathic pain. In this example, tissues from the spinal cord were obtained from animals which have been stimulated using a rectangular waveform at a frequency of 50 Hz and a pulse width of 200 μs per phase which were either monophasic cathodic, monophasic anodic, or symmetric biphasic with an initial cathodic polarity. RNA from tissues was extracted and transcribed into DNA using standard PCR techniques. The amount of DNA was then quantified and standardized. Based on our previous experiments (example 2) a panel of genes including markers for glial activation (tlr2, cxcl16), calcium-dependent glial processes (cabp1), immune system activation (cd68), and an opioid receptor (oprm1) were selected for analysis.

FIGS. 32(a)-(e) illustrate conceptually graphs of expression of selected genes relative to the polarity of the phase used in the stimulation waveform, including a) Calcium binding protein (cabp1); b) Chemokine cxcl16; c) Toll-like receptor 2 (tlr2); d) Cd68 molecule; and e) Opioid receptor mu-1 (oprm1). It is evident that the polarity of the signal phase influences the activation (tlr2 and cxcl16) relative to anodic and cathodic stimulation in response to the release of glutamate from astrocytes. Biphasic stimulation increases the amount of cabp1 relative to monophasic stimulation (cathodic or anodic). Monophasic stimulation (cathodic or anodic) and biphasic stimulation produces similar amounts of the immune-related gene cd 68 and expression of the gene coding for the opioid receptor, oprm1.

EXAMPLE 4

The subject patient was a 55 y/o female patient with diagnosis of Failed Back Surgery Syndrome complaining of severe axial low back pain radiating to bilateral lower extremities all the way to the feet for over eight years. Patient failed multiple medical treatments including physical therapy, medication management and surgical intervention.

The patient underwent a spinal cord stimulator trial with a conventional SCS system. Two leads were positioned in the posterior epidural space with the tip of the leads located at the junction of T7 and TS. Patient returned two days later for reprogramming as leads migrated down as confirmed by x-ray fluoroscopy. After lead repositioning, patient reported paresthesia coverage from torso level down to leg while in prone position. Reprogramming took place while subject was seating/standing; however patient reported no coverage on back. Treatment seemed to only cover from waist down to legs. Multiple attempts failed to improve the outcome. At the conclusion of the trial with conventional SCS, the patient reported only 25% relief.

At this point, the multimodal stimulation system was applied with prime modality as described herein. The system was reprogrammed using two external generators. One was set at 70 Hz, 700 μs PW in the upper contacts of the parallel leads. The other was set for priming at 1,000 Hz, 200 μs PW. The patient reported block of paresthesia when the 1,000 Hz was on, while the amplitude of the 70 Hz was 3 mA. Amplitude was increased slowly until 3.6-3.7 mA when she experienced paresthesia. Amplitude of the 1,000 Hz signal was set at 2 mA when patient went home. Patient reported no pain in the back.

Patient returned two days later for reprogramming of the multimodal stimulation. After reprogramming, patient continued experiencing pain relief without tingling. Particularly important is pain relief in the back. Pain relief was also experienced in the legs, but not in the feet. Paresthesia was also perceived at 3.7 mA when the 1,000 Hz stimulation was on, and 3.0 mA when was off. Amplitude of the 1,000 Hz signal was set below 2 mA, which is below the PPT. Patient went home with 2 mA at 1,000 Hz and 2.9 mA at 70 Hz. Patient was able to walk well, flex downward and reported immediate pain relief in the back.

Patient returned four days later. Subject had adjusted the amplitude of the 1,000 Hz down to 1.7 mA because she felt muscle fatigue in the back. The amplitude of the 70 Hz was set at 2.3 mA.

In summary of trial:
1. Subject patient did not experienced paresthesias during the four days of treatment.
2. Patient reported that the Multimodal Prime treatment was superior to Tonic treatment.
3. Patient reported no back pain.
4. Sharp/stabbing pain in leg was significantly reduced.
5. Burning sensation in the feet was not alleviated which prevented patient from long walks.
6. Significant reduction in opioid consumption.
7. She reported about overall 70% pain relief with multimodal stimulation.

EXAMPLE 5

The subject patient was a 70 y/o male diagnosed with radiculopathy. Patient has suffered from condition since for about 17 years. Subject has been treated with conventional treatments without clinical success. Pain numerical rate score before treatment was reported as 10, with pain in the back radiating to the legs. A pair of SCS trial leads were implanted using a non-parallel alignment (i.e. they were offset from each other), and a tonic program has been set. Patient reported 70-75% pain relief in the back and 80% pain relief in the leg from the conventional treatment. Patient reported improvement in sleep and a decrease of Vicodin ingestion. Subject reported liking the paresthesia sensation relative to experiencing pain. Patient reported that discomfort in left foot was not being eliminated by treatment.

Patient was then reprogrammed using multimodal stimulation with a prime arrangement with a priming parameters set at 1,200 Hz, 150 μs PW and 5.5 mA, while low frequency parameters were set at 50 Hz, 400 μs PW and 3.2 mA. Patient experienced paresthesia at 3.5 mA.

Patient did not experience pain in back and legs during the following couple of days and was able to adjust low frequency up and down as he felt comfortable with the paresthesias. However, he maintained the amplitude below the paresthesia threshold for most of the time.

In the evening the next day, patient was very active climbing up and down stairs (an activity he avoided before SCS treatment). Family was impressed he could walk as much as he did that day. On the following day he was active around the house doing some activities in his yard, particularly handling the garbage. He admitted he overdid activities in the last couple of days and thus reported pain at night. He ingested 1 Vicodin and increased level of low frequency signal to paresthesia sensation and turned it down to go to sleep. He slept well for 7 hours-. Previous nights he had slept very well for about 8-9 hours. On the afternoon of the following day, he reported no pain (score of 0) in both back and leg and no discomfort or pain in the feet.

Patient likes the fact he can feel paresthesias for reassuring his pain relief, but enjoys being able to have pain relief without having the constant tingling. Patient was disappointed he was not going to have the multimodal treatment option when permanently implanted.

In summary:
1. Patient did not experience paresthesias most of the time during three days. He adjusted amplitude of low frequency tonic stimulator to feel paresthesia when pain recurred and adjusted amplitude down to paresthesia-free to maintain pain relief.
2. Patient was able to reduce pain medication ingestion.
3. Patient reported no back pain and no pain in leg and feet. He reported 100% relief with prime, except when he increased his daily activity considerably relative to usual one he had before stimulation.
4. Patient reported significant improvement on sleep habits.
5. Patient indicated he likes the ability of set paresthesia as a way of reaffirming a stimulation dosage that will guarantee pain relief when amplitude is then turned down below paresthesia while maintaining pain relief.

EXAMPLE 6

Figure 17A:
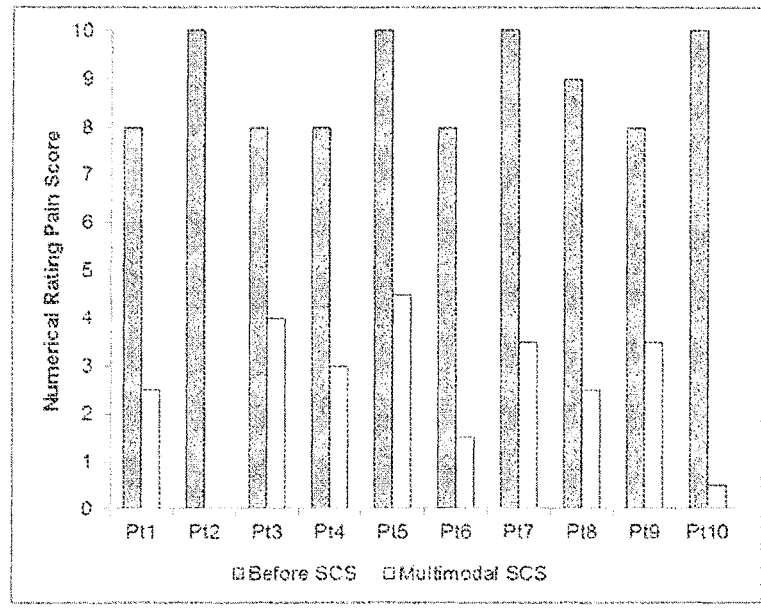
FIGS. 17A-B illustrate conceptually graphs of results achieved in a short time pilot clinical trial period utilizing systems and methods in accordance with the present disclosure.
Figure 17B:
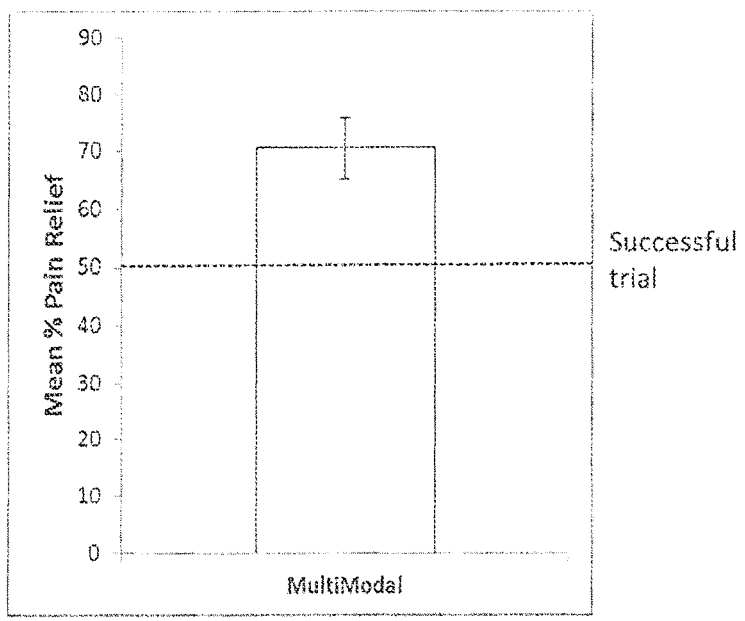

Referring to FIGS. 17A-B, an observational study using human volunteers was carried out (n=10). These subjects were part of a trial period for commercial spinal cord stimulation systems administered under standard clinical practice. Subjects voluntarily accepted to try multimodal modulation after they had completed their trial period. Success in a trial period is indicated by pain relief equal or above 50% relative to the pain numerical rating score (NRS) present before the spinal cord stimulation therapy was commenced. All subjects had been implanted with two eight-electrode trial leads. Six of them had leads staggered relative to each other and four of them had leads parallel to each other. Five of the subjects had trialed conventional tonic stimulation systems (50-70 Hz) and five of them had trialed a high frequency system (10,000 Hz). Two of the subjects failed the trial with conventional tonic stimulation (50-70 Hz). Nine of the subjects tried multimodal stimulation using the prime modality and one of them tried the twin modality. Multimodal stimulation was tried for as short as 3 hours and for as long as 4 days. All the ten subjects successfully tried multimodal stimulation under the paresthesia or perception threshold (PT). The mean pain relief of the subjects was 71% and all subjects declared to be satisfied with multimodal stimulation therapy.

The reader will appreciate that the multimodal modulation techniques described herein, including the Prime and Twin modulation techniques, as well as modulation achieved with a composite signal, e.g. frequency, amplitude, or pulse width modulated, and multi-modal modulation, can be utilized for regulation of genes and proteins that modulate the interactions between glial cells and neurons as described herein.

As used herein, the term "pharmacological substance" means any tangible chemical, drug, medicine or therapeutic substance, either synthetic or naturally occurring, regardless of the form of administration to the subject, that is administered to the body of the subject.

At various places in the present specification, values are disclosed in groups or in ranges. It is specifically intended that the description include each and every individual subcombination of the members of such groups and ranges and any combination of the various endpoints of such groups or ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

For purposes of clarity and a concise description, features are described herein as part of the same or separate embodiments, however, it will be appreciated that scope of the concepts may include embodiments having combinations of all or some of the features described herein.

It will be obvious to those recently skilled in the art that modifications to the apparatus and process disclosed here in may occur, including substitution of various component values or nodes of connection, without parting from the true spirit and scope of the disclosure as defined by the claims set forth herein. For example, although the embodiments described herein disclose primarily the use of pulsed rectangular signals, other waveform shapes may be similarly used to obtain the same effects. For example, any of a monophasic pulse wave, charge balanced biphasic pulse wave, charge imbalanced biphasic pulse wave, charge balanced biphasic with delay pulse wave, charge balanced biphasic fast reversal wave, and charge balanced biphasic slow reversal wave may be utilized as stimulating waveforms in the multimodal modulation techniques described herein. In addition, other varying electromagnetic fields defined by periodic electric signals having different waveform shapes may be used as well as noise signals and even non-periodic electric signals having irregular nonrepeating shapes.

What is claimed is:

1. A method comprising:
stimulating glial cells of a subject with a first electromagnetic stimulus and simultaneously and differentially stimulating neurons of the subject with a second electromagnetic stimulus having a different electrical parameter than the first electromagnetic stimulus,
providing a priming signal to a first subgroup of a plurality of electrodes and simultaneously providing a tonic signal to a second subgroup of the plurality of electrodes,
wherein the priming signal and the tonic signal have at least one uncommon parameter therebetween, and
wherein characteristics of the first electromagnetic stimulus and the second electromagnetic stimulus control any of glial depolarization, release or uptake of ions, or release of glial transmitters by the glial cells.

2. The method of claim 1, wherein the priming signal and tonic signal are provided by at least a first electric signal source and a second electric signal source,
wherein the first subgroup of the plurality of electrodes is electrically coupled to the first electric signal source, and
wherein the second subgroup of the plurality of electrodes is electrically coupled to the second electric signal source.

3. The method of claim 1, wherein the priming signal and the tonic signal have any of different respective amplitudes, frequencies, relative phases, waveform shapes, or widths.

4. The method of claim 1, wherein the first electromagnetic stimulus is generated by the priming signal and the second electromagnetic stimulus is generated by the tonic signal.

5. The method of claim 1, wherein both the priming and tonic signals have different respective frequencies below 1,500 Hz.

6. The method of claim 1, wherein one of the priming and tonic signals has a frequency below the other of the priming and tonic signals.

7. The method of claim 1, wherein the priming signal comprises one of a monophasic electrical signal or a biphasic electrical signal.

8. The method of claim 1, wherein the tonic signal comprises one of a monophasic electrical signal or a biphasic electrical signal.

9. The method of claim 1, wherein the priming signal has a frequency of between 200 Hz and 1500 Hz.

10. The method of claim 1, wherein the tonic signal has a frequency of between 20 Hz and 150 Hz.

11. The method of claim 10, wherein the priming signal has a frequency that is higher than the tonic signal.

12. The method of claim 11, wherein the priming signal has a frequency of between 200 Hz and 1500 Hz.

13. The method of claim 1, wherein the tonic signal has a frequency of 50 Hz.

14. The method of claim 13, wherein the priming signal has a frequency that is higher than the tonic signal.

15. The method of claim 14, wherein the priming signal has a frequency of between 200 Hz and 1500 Hz.

16. The method of claim 1, wherein the first electromagnetic stimulus and the second electromagnetic stimulus are provided by one or more electrodes of the plurality of electrodes connected to a signal generation module.

17. The method of claim 16, wherein the one or more electrodes comprises the first subgroup and the second subgroup of the plurality of electrodes.

18. The method of claim 17, wherein the first subgroup of the plurality of electrodes generates the first electromagnetic stimulus and wherein the second subgroup of the plurality of electrodes generates the second electromagnetic stimulus.

19. The method of claim 16, wherein the signal generation module comprises a multimodal signal generator controllable by one of a plurality of multimodal signal parameter programs and configured for simultaneously generating the first electromagnetic stimulus the second electromagnetic stimulus.

20. The method of claim 19, further comprising selecting, by a selection device, one of a plurality of multimodal signal parameter programs stored in memory.

* * * * *